(12) United States Patent
Starobin et al.

(10) Patent No.: US 6,656,126 B2
(45) Date of Patent: *Dec. 2, 2003

(54) METHOD AND SYSTEM FOR EVALUATING CARDIAC ISCHEMIA WITH RR-INTERVAL DATA SETS AND PULSE OR BLOOD PRESSURE MONITORING

(75) Inventors: Joseph M. Starobin, Greensboro, NC (US); Yuri B. Chernyak, Lexington, MA (US)

(73) Assignee: MediWave Star Technology, Inc., Greensboro, NC (US)

( * ) Notice: Subject to any disclaimer, the term of this patent is extended or adjusted under 35 U.S.C. 154(b) by 8 days.

This patent is subject to a terminal disclaimer.

(21) Appl. No.: 10/035,951

(22) Filed: Dec. 26, 2001

(65) Prior Publication Data

US 2002/0165460 A1 Nov. 7, 2002

Related U.S. Application Data

(63) Continuation-in-part of application No. 09/891,910, filed on Jun. 26, 2001, which is a continuation-in-part of application No. 09/603,286, filed on Jun. 26, 2000, now Pat. No. 6,361,503.

(51) Int. Cl.[7] ............................................. A61B 5/0452
(52) U.S. Cl. ....................................................... 600/508
(58) Field of Search ................................. 600/508–510, 600/515–521

(56) References Cited

U.S. PATENT DOCUMENTS

| | | | |
|---|---|---|---|
| 4,870,974 A | 10/1989 | Wang | 128/700 |
| 5,020,540 A | 6/1991 | Chamoun | 128/703 |
| 5,117,834 A | 6/1992 | Kroll et al. | 128/705 |
| 5,148,812 A | 9/1992 | Verrier et al. | 128/704 |
| 5,323,783 A | 6/1994 | Henkin et al. | 128/703 |
| 5,419,338 A | 5/1995 | Sarma et al. | 128/703 |
| 5,560,370 A | 10/1996 | Verrier et al. | 128/705 |
| 5,713,367 A | 2/1998 | Arnold et al. | 128/704 |
| 5,792,065 A | 8/1998 | Xue et al. | 600/516 |
| 5,794,623 A | 8/1998 | Forbes | 128/702 |
| 5,827,195 A | 10/1998 | Lander | 600/509 |
| 5,842,997 A | 12/1998 | Verrier et al. | 600/518 |
| 5,891,047 A | 4/1999 | Lander et al. | 600/516 |
| 5,921,940 A | 7/1999 | Verrier et al. | 600/518 |
| 5,951,484 A | 9/1999 | Hoium et al. | 600/515 |
| 6,361,503 B1 * | 3/2002 | Starobin et al. | 600/508 |

OTHER PUBLICATIONS

Sarma et al, "Hysteresis. . . Recovery", May–Jun. 1987.*
Arnold et al.; *The dependence on heart rate of the human ventricular action potential duration*, Cardiovascular Research, 16, 547–551 (1982).
Chernyak et al.; *Class of Exactly Solvable Models of Excitable Media*, Phys. Rev. Lett., 80:25, 5675–5678 (1998).

(List continued on next page.)

Primary Examiner—George R. Evanisko
(74) Attorney, Agent, or Firm—Myers Bigel Sibley & Sajovec

(57) ABSTRACT

A method of assessing cardiac ischemia in a subject to provide a measure of cardiac or cardiovascular health in that subject is described herein. The method comprises the steps of: (a) collecting a first RR-interval data set from the subject during a stage of gradually increasing heart rate (e.g., a stage of gradually increasing exercise load); (b) collecting a second RR-interval data set from the subject during a stage of gradually decreasing heart rate (e.g., a stage of gradually decreasing exercise load); (c) comparing the first RR-interval data set to the second RR-interval data set to determine the difference between the data sets; and (d) generating from the comparison of step (c) a measure of cardiac ischemia during exercise in the subject. A greater difference between the first and second data sets indicates greater cardiac ischemia and lesser cardiac or cardiovascular health in the subject. The data sets may be collected by any suitable method or device, including pulse monitoring and blood pressure monitoring.

56 Claims, 20 Drawing Sheets

OTHER PUBLICATIONS

Chernyak et al.; *Where do dispersion curves end? A basic question in theory of excitable media*, Phys. Rev. E,. 58:4, 4108–4111 (1998).

Ciavolella et al.; *Exponential Fit of QT Interval–Heart Rate Relation During Exercise Used to Diagnose Stress–induced Myocardial Ischemia*, Journal of Electrocardiology, 24:2, 145–153 (1991).

Cole et al.; *Heart–Rate Recovery Immediately After Exercise As A Predictor Of Mortality*, The New England Journal of Medicine, 341:18, 1351–1357 (Oct. 1999).

Franz et al.; *Cycle Length Dependence of Human Action Potential Duration In Vivo; Effects of Single Extrastimuli, Sudden Sustained Rate Acceleration and Deceleration, and Different Steady–State Frequencies*, J. Clin. Invest,. 82, 972–979 (1988).

Froelicher, Jr. et al.; *A comparison of three maximal treadmill exercise protocols*, Journal of Applied Physiology, 36:6, 720–725 (1974).

Hintze et al.; *Prognostic Properties of QT/RR Dynamics in Survivors of Myocardial Infarction with Reduced Systolic Function*, NASPE Annual Meeting, Washington, D.C. (May 17–20, 2000).

Jonnalegedda et al.; *An Exponential Formula for Heart Rate Dependence of QT Interval During Exercise and Cardiac Pacing in Humans: Reevaluation of Bazett's Formula*, Am J Cardiol, 54, 103–108 (1984).

Jonnalegedda et al.; *Hysteresis in the Human RR–QT Relationship During Exercise and Recovery*, PACE 10, 485–491 (1997).

Krahn, M.D. et al.; *Hysteresis of the RT Interval With Exercise; A New Marker for the Long–QT Syndrome?*, Circulation, 96, 1551–1556 (1997).

Lau et al.; *Hysteresis of the ventricular paced QT interval in response to abrupt changes in pacing rate*, Cardiovascular Research 22, 67–72 (1988).

Starobin et al.; *The role of a critical excitation length scale in dynamics of reentrant cardiac arrhythmias*, Herzschr Elektrophys, 10, 119–136 (Month Unknown, 1999).

Surawicz; *Will QT Dispersion Play a Role in Clinical Decision–Making?*, J Cardiovascular Electrophysiol, 7, 777–784 (1996).

Swan et al.; *Rate adaption of QT intervals during and after exercise in children with congenital long QT syndrome*, European Heart Journal, 19, 508–513 (1998).

Takahashi et al.; *Paradoxically Shortened QT Interval after a Prolonged Pause*, PACE, 21, 1476–1479 (1998).

Pierpoint et al.; *Heart rate recovery post–exercise as an index of parasympathetic activity*, Journal of the Autonomic Nervous System, 80, 169–174 (May 12, 2000).

International Search Report, International Application No. PCT/US01/20391 dated Aug. 20, 2001.

\* cited by examiner $$\frac{\partial u}{\partial t} = \frac{\partial^2 u}{\partial x^2} - i(u,v)$$

$$\frac{\partial v}{\partial t} = \varepsilon g(u,v)$$

(A)

(B)

(C)

METHOD AND SYSTEM FOR EVALUATING CARDIAC ISCHEMIA WITH RR-INTERVAL DATA SETS AND PULSE OR BLOOD PRESSURE MONITORING

RELATED APPLICATIONS

This application is a continuation-in-part of copending application Ser. No. 09/891,910, filed Jun. 26, 2001, which in turn is a continuation-in-part of application Ser. No. 09/603,286, filed Jun. 26, 2000, now U.S. Pat. No. 6,361,503 the disclosures of both of which are incorporated by reference herein in their entirety.

FIELD OF THE INVENTION

The present invention relates to non-invasive high-resolution diagnostics of cardiac ischemia based on processing of data such as body-surface electrocardiogram (ECG) data, or other pulse or blood pressure data. The invention's quantitative method of assessment of cardiac ischemia may simultaneously indicate both cardiac health itself and cardiovascular system health in general.

BACKGROUND OF THE INVENTION

Heart attacks and other ischemic events of the heart are among the leading causes of death and disability in the United States. In general, the susceptibility of a particular patient to heart attack or the like can be assessed by examining the heart for evidence of ischemia (insufficient blood flow to the heart tissue itself resulting in an insufficient oxygen supply) during periods of elevated heart activity. Of course, it is highly desirable that the measuring technique be sufficiently benign to be carried out without undue stress to the heart (the condition of which might not yet be known) and without undue discomfort to the patient.

The cardiovascular system responds to changes in physiological stress by adjusting the heart rate, which adjustments can be evaluated by measuring the surface ECG R—R intervals. The time intervals between consecutive R waves indicate the intervals between the consecutive heartbeats (RR intervals). This adjustment normally occurs along with corresponding changes in the duration of the ECG QT intervals, which characterize the duration of electrical excitation of cardiac muscle and represent the action potential duration averaged over a certain volume of cardiac muscle (FIG. 1). Generally speaking, an average action potential duration measured as the QT interval at each ECG lead may be considered as an indicator of cardiac systolic activity varying in time.

Recent advances in computer technology have led to improvements in automatic analyzing of heart rate and QT interval variability. It is well known now that the QT interval's variability (dispersion) observations performed separately or in combination with heart rate (or RR-interval) variability analysis provides an effective tool for the assessment of individual susceptibility to cardiac arrhythmias (B. Surawicz, J. Cardiovasc. Electrophysiol, 1996, 7, 777–784). Applications of different types of QT and some other interval variability to susceptibility to cardiac arrhythmias are described in U.S. Patents by Chamoun U.S. Pat. No. 5,020,540, 1991; Wang U.S. Pat. No. 4,870,974, 1989; Kroll et al. U.S. Pat. No. 5,117,834, 1992; Henkin et al. U.S. Pat. No. 5,323,783, 1994; Xue et al. U.S. Pat. No. 5,792,065, 1998; Lander U.S. Pat. No. 5,827,195, 1998; Lander et al. U.S. Pat. No. 5,891,047, 1999; Hojum et al. U.S. Pat. No. 5,951,484, 1999).

It was recently found that cardiac electrical instability can be also predicted by linking the QT-dispersion observations with the ECG T-wave alternation analysis (Verrier et al., U.S. Pat. Nos. 5,560,370; 5,842,997; 5,921,940). This approach is somewhat useful in identifying and managing individuals at risk for sudden cardiac death. The authors report that QT interval dispersion is linked with risk for arrhythmias in patients with long QT syndrome. However, QT interval dispersion alone, without simultaneous measurement of T-wave alternation, is said to be a less accurate predictor of cardiac electrical instability (U.S. Pat. No. 5,560,370 at column 6, lines 4–15).

Another application of the QT interval dispersion analysis for prediction of sudden cardiac death is developed by J. Sarma (U.S. Pat. No. 5,419,338). He describes a method of an autonomic nervous system testing that is designed to evaluate the imbalances between both parasympathetic and sympathetic controls on the heart and, thus, to indicate a predisposition for sudden cardiac death.

The same author suggested that an autonomic nervous system testing procedure might be designed on the basis of the QT hysteresis (J. Sarma et al., *PACE* 10, 485–491 (1988)). Hysteresis between exercise and recovery was observed, and was attributed to sympatho-adrenal activity in the early post-exercise period. Such an activity was revealed in the course of QT interval adaptation to changes in the RR interval during exercise with rapid variation of the load.

The influence of sympatho-adrenal activity and the sharp dependence of this hysteresis on the time course of abrupt QT interval adaptation to rapid changes in the RR interval dynamics radically overshadows the method's susceptibility to the real ischemic-like changes of cardiac muscle electrical parameters and cardiac electrical conduction. Therefore, this type of hysteresis phenomenon would not be useful in assessing the health of the cardiac muscle itself, or in assessing cardiac ischemia.

A similar sympatho-adrenal imbalance type hysteresis phenomenon was observed by A. Krahn et al. (*Circulation* 96, 1551–1556 (1997)(see FIG. 2 therein)). The authors state that this type of QT interval hysteresis may be a marker for long-QT syndrome. However, long-QT syndrome hysteresis is a reflection of a genetic defect of intracardiac ion channels associated with exercise or stress-induced syncope or sudden death. Therefore, similar to the example described above, although due to two different reasons, it also does not involve a measure of cardiac ischemia or cardiac muscle ischemic health.

A conventional non-invasive method of assessing coronary artery diseases associated with cardiac ischemia is based on the observation of morphological changes in a surface electrocardiogram during physiological exercise (stress test). A change of the ECG morphology, such as an inversion of the T-wave, is known to be a qualitative indication of ischemia. The dynamics of the ECG ST-segments are continuously monitored while the shape and slope, as well as ST-segment elevation or depression, measured relative to an average base line, are altering in response to exercise load. A comparison of any of these changes with average values of monitored ST segment data provides an indication of insufficient coronary blood circulation and developing ischemia. Despite a broad clinical acceptance and the availability of computerized Holter monitor-like devices for automatic ST segment data processing, the diagnostic value of this method is limited due to its low sensitivity and low resolution. Since the approach is specifically reliable primarily for ischemic events associated with relatively high coronary artery occlusion, its widespread use often results in false positives, which in turn may lead to unnecessary and more expensive, invasive cardiac catheterization.

Relatively low sensitivity and low resolution, which are fundamental disadvantages of the conventional ST-segment depression method, are inherent in such method's being based on measuring an amplitude of a body surface ECG signal, which signal by itself does not accurately reflect changes in an individual cardiac cell's electrical parameters normally changing during an ischemic cardiac event. A body surface ECG signal is a composite determined by action potentials aroused from discharge of hundred of thousands of individual excitable cardiac cells. When electrical activity of excitable cells slightly and locally alters during the development of exercise-induced local ischemia, its electrical image in the ECG signal on the body surface is significantly overshadowed by the aggregate signal from the rest of the heart. Therefore, regardless of physiological conditions, such as stress or exercise, conventional body surface ECG data processing is characterized by a relatively high threshold (lower sensitivity) of detectable ischemic morphological changes in the ECG signal. An accurate and faultless discrimination of such changes is still a challenging signal processing problem.

Accordingly, an object of the present invention is to provide a non-invasive technique for detecting and measuring cardiac ischemia in a patient.

Another object of the invention is to provide a technique for detecting and measuring cardiac ischemia, which technique is not unduly uncomfortable or stressful for the patient.

Another object of the invention is to provide a technique for detecting and measuring cardiac ischemia, which technique may be implemented with relatively simple equipment.

Still another object of the invention is to provide a technique for detecting and measuring cardiac ischemia, which technique is sensitive to low levels of such ischemia.

SUMMARY OF THE INVENTION

The present invention overcomes the deficiencies in the conventional ST-segment analysis. Although still based on the processing of a body surface ECG signal, it nevertheless provides a highly sensitive and high resolution method for distinguishing changes in cardiac electrical conduction associated with developing cardiac ischemia. In addition to the significant cardiac ischemic changes detectable by the conventional method, the present invention allows one to determine much smaller ischemia-induced conditions and alterations in cardiac electrical conduction. Thus, unlike a conventional ST-segment depression ischemic analysis, the method of the present invention opens up opportunities to detect low-level cardiac ischemia (undetectable via the regular ST-segment method) and also to resolve and monitor small variations of cardiac ischemia. In particular, individuals who would be considered of the same level of cardiac and cardiovascular health according to a conventional ECG evaluation (an ST-depression method), will have different measurements if compared according to the method of the present invention, and the cardiac and cardiovascular health of an individual can be quantitatively evaluated, compared and monitored by repeated applications of the method of the present invention.

The present invention is based in part on the discovery that, under certain physiological conditions, QT- and/or RR-interval data sets may be interpreted as representing composite dispersion-restitution curves, which characterize the basic dynamic properties of the medium (in this case, cardiac muscle). Indeed, if rapid interval adaptation facilitated by sympatho-adrenal activity occurs much faster than gradual heart rate changes following slow alteration of external physiological conditions, then the interval may be considered primarily as a function of a heart rate and/or a preceding cardiac cycle length and does not substantially depend on time-dependent sympatho-adrenal transients. In such a case a particular interval data set determines a time-independent, dispersion-like, quasi-stationary curve which does not substantially depend on rapid adaptational transients and depends primarily on medium electrical parameters.

Based on this discovery, the present invention provides a highly sensitive and high resolution method of assessing cardiac ischemia. This method allows one to detect comparatively small alterations of cardiac muscle electrical excitation properties that develop during even a moderate ischemic condition. For example, consider a gradual heart rate adjustment in a particular human subject in response to slow (quasi-stationary), there-and-back changes of external physiological conditions. Ideally, when a cardiac muscle is supplied by a sufficient amount of oxygen during both gradually increasing and gradually decreasing heart rate stages, the corresponding, there-and-back, quasi-stationary interval curves which result should be virtually identical. However, if ischemia exists, even if only to a very minor extent, there will be alterations of cardiac muscle repolarization and excitation properties for the human subject with the result that one observes a specific quasi-stationary hysteresis loop. Unlike non-stationary loops (J. Sarma et al., supra (1987); A. Krahn et al., supra (1997)), the quasi-stationary hystereses of the present invention do not vary substantially versus the course of sympatho-adrenal interval adjustment. The domains and shapes of these loops are not significantly affected by time-dependent transients rapidly decaying during a transition from one particular heart rate to another; instead, they depend primarily on ischemia-induced changes of medium parameters. The domain encompassed by such a quasi-stationary hysteresis loop and its shape represent a new quantitative characteristics that indicate cardiac muscle health itself and the health of the cardiovascular system in general. Moreover, any measure of the shape and/or domain enclosed in the hysteresis loop (a measure of a set as defined in the integral theory) possesses the property that any expansion of the domain results in an increase of the measure. Any such mathematical measure can be taken as the new characteristics of cardiac health mentioned above. An arbitrary monotonic function of such a measure would still represent the same measure in another, transformed scale.

A first aspect of the present invention is a method of assessing cardiac ischemia in a subject to provide a measure of cardiovascular health in that subject. The method comprises the steps of:

(a) collecting a first RR-interval data set (e.g, a first QT- and RR-interval data set) from the subject during a stage of gradually increasing heart rate;

(b) collecting a second RR-interval data set (e.g., a second QT- and RR-interval data set) from the subject during a stage of gradually decreasing heart rate;

(c) comparing said first interval data set to the second interval data set to determine the difference between the data sets; and (d) generating from the comparison of step (c) a measure of cardiac ischemia during exercise in said subject, wherein a greater difference between said first and second data sets indicates greater cardiac ischemia and lesser cardiovascular health in said subject.

During the periods of gradually increasing and gradually decreasing heart rate the effect of the sympathetic, parasympathetic, and hormonal control on formation of the hysteresis loop is sufficiently small, minimized or controlled so that the ischemic changes are readily detectable. This maintenance is achieved by effecting a gradual increase and gradual decrease in the heart rate, such as, for example, by controlling the heart rate through pharmacological intervention, by direct electrical stimulation of the heart, or by gradually increasing and gradually decreasing exercise loads.

Accordingly, the foregoing method can be implemented in a variety of different ways. A particular embodiment comprises the steps of:

(a) collecting a first RR-interval data set (e.g., a first QT- and RR-interval data set) from said subject during a stage of gradually increasing exercise load and gradually increasing heart rate;

(b) collecting a second RR-interval data set (e.g., a second QT- and RR-interval data set) from said subject during a stage of gradually decreasing exercise load and gradually decreasing heart rate;

(c) comparing the interval data set to the second interval data set to determine the difference between said data sets; and (d) generating from said comparison of step (c) a measure of cardiac ischemia during exercise in said subject, wherein a greater difference between said first and second data sets indicates greater cardiac ischemia and lesser cardiovascular health in said subject.

A second aspect of the present invention is a system for assessing cardiac ischemia in a subject to provide a measure of cardiovascular health in that subject. The system comprises:

(a) an ECG recorder for collecting a first RR-interval data set (e.g., a first QT- and RR-interval data set) from the subject during a stage of gradually increasing heart rate and collecting a second RR-interval data set (e.g. a second QT- and RR-interval data) set from the subject during a stage of gradually decreasing heart rate;

(b) a computer program running in a computer or other suitable means for comparing said first interval data set to the second interval data set to determine the difference between the data sets; and (c) a computer program running in a computer or other suitable means for generating from said determination of the difference between the data sets a measure of cardiac ischemia during exercise in said subject, wherein a greater difference between the first and second data sets indicates greater cardiac ischemia and lesser cardiovascular health in the subject.

A further aspect of the present invention is a method of assessing cardiac ischemia in a subject to provide a measure of cardiac or cardiovascular health in that subject, the method comprising the steps, performed on a computer system, of:

(a) providing a first RR-interval data set (e.g., a first QT- and RR-interval data set) collected from the subject during a stage of gradually increasing heart rate;

(b) providing a second RR-interval data set (e.g., a second QT- and RR-interval data set) collected from the subject during a stage of gradually decreasing heart rate;

(c) comparing the first interval data set to the second interval data set to determine the difference between the data sets; and (d) generating from the comparison of step (c) a measure of cardiac ischemia during stimulation in the subject, wherein a greater difference between the first and second data sets indicates greater cardiac ischemia and lesser cardiac or cardiovascular health in the subject.

The first and second interval data sets may be collected while minimizing the influence of rapid transients due to autonomic nervous system and hormonal control on the data sets. The first and second interval data sets are collected without an intervening rest stage. The generating step may be carried out by generating curves from each of the data sets, and/or the generating step may be carried out by comparing the shapes of the curves from data sets. In a particular embodiment, the generating step is carried out by determining a measure of the domain between the curves. In another particular embodiment, the generating step is carried out by both comparing the shapes of the curves from data sets and determining a measure of the domain between the curves. The method may include the further step of displaying the curves. In one embodiment the comparing step may be carried out by: (i) filtering the first and second interval data sets; (ii) generating a smoothed hysteresis loop from the filtered first and second interval data sets; and then (iii) determining a measure of the domain inside the smoothed hysteresis loop. In another embodiment, the comparing step may be carried out by: (i) filtering the first and second interval data sets; (ii) generating preliminary minimal values for the first and second interval data sets; (iii) correcting the preliminary minimal values; (iv) generating first and second preliminary smoothed curves from each of the filtered data sets; (v) correcting the preliminary smoothed curves; (vi) fitting the preliminary smoothed curves; (vii) generating a smoothed hysteresis loop from the first and second fitted smoothed curves; and then (viii) determining a measure of the domain inside the hysteresis loop. In still another embodiment, the comparing step is carried out by: (i) filtering the first and second interval data sets by moving average smoothing; (ii) generating a smoothed hysteresis loop from the filtered first and second interval data sets; and then (iii) determining a measure of the domain inside the hysteresis loop.

A further aspect of the present invention is a computer system for assessing cardiac ischemia in a subject to provide a measure of cardiac or cardiovascular health in that subject, the system comprising:

(a) means for providing a first RR-interval data set (e.g., a first QT- and RR-interval data set) from the subject during a stage of gradually increasing heart rate;

(b) means for providing a second RR-interval data set (e.g., a second QT- and RR-interval data set) from the subject during a stage of gradually decreasing heart rate;

(c) means for comparing the first interval data set to the second interval data set to determine the difference between the data sets; and (d) means for generating from the comparison of step (c) a measure of cardiac ischemia during stimulation in the subject, wherein a greater difference between the first and second data sets indicates greater cardiac ischemia and lesser cardiac or cardiovascular health in the subject.

A still further aspect of the present invention is a computer program product for assessing cardiac ischemia in a subject to provide a measure of cardiac or cardiovascular health in that subject, the computer program product comprising a computer usable storage medium having computer readable program code means embodied in the medium, the computer readable program code means comprising:

(a) computer readable program code means for comparing a first KR-interval data set (e.g., a first QT- and RR-interval data set) to a second RR-interval data set (e.g., a second QT- and RR-interval data set) to determine the difference between the data sets; and (b) computer readable program code means for generating from the comparison of step (c) a measure of cardiac ischemia during stimulation in the subject, wherein a greater difference between the first and second data sets indicates greater cardiac ischemia and lesser cardiac or cardiovascular health in the subject.

While the present invention is described herein primarily with reference to the use of QT- and RR-interval data sets, it will be appreciated that the invention may be implemented in simplified form with the use of RR-interval data sets alone. For use in the claims below, it will be understood that the term "RR-interval data set" is intended to be inclusive of both the embodiments of QT- and RR-interval data sets and RR-interval data sets alone, unless expressly subject to the proviso that the data set does not include a QT-interval data set.

The present invention is explained in greater detail in the drawings herein and the specification set forth below.

DETAILED DESCRIPTION OF THE PREFERRED EMBODIMENTS

Figure 1:
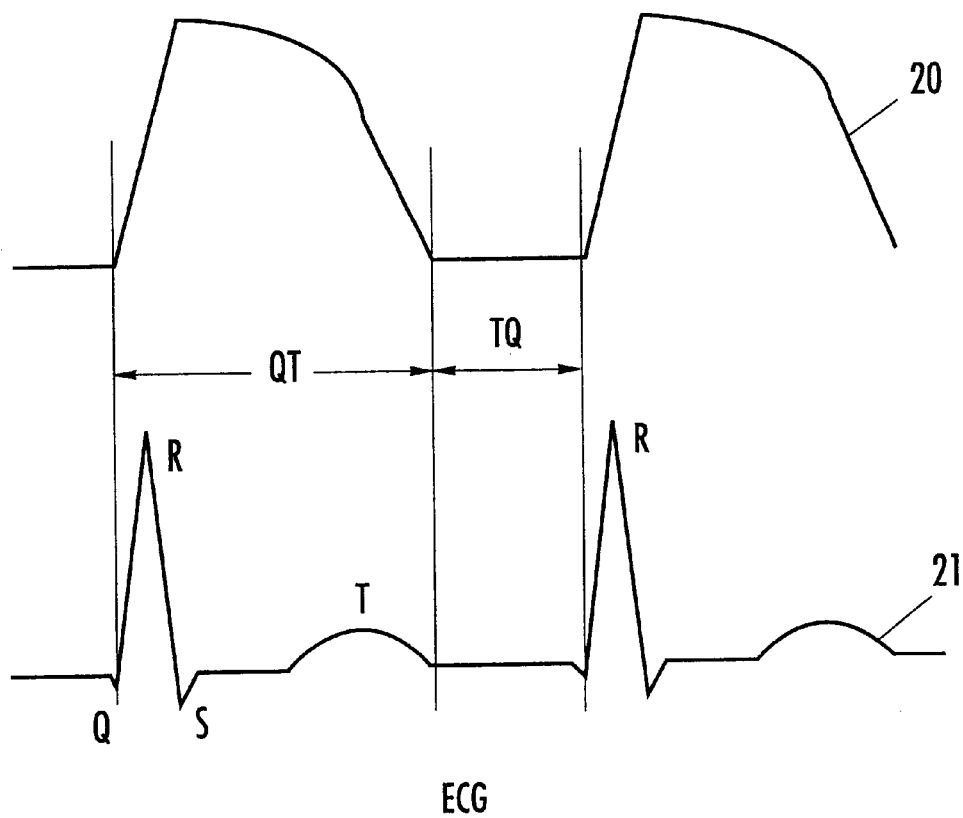
FIG. 1 is a schematic graphic representation of the action potential in cardiac muscle summed up over its volume and the induced electrocardiogram (ECG) recorded on a human's body surface.

The present invention is explained in greater detail below. This description is not intended to be a detailed catalog of all the different manners in which particular elements of the invention can be implemented, and numerous variations will be apparent to those skilled in the art based upon the instant disclosure.

As will be appreciated by one of skill in the art, certain aspects of the present invention may be embodied as a method, data processing system, or computer program product. Accordingly, certain aspects of the present invention may take the form of an entirely hardware embodiment, an entirely software embodiment, or an embodiment combining software and hardware aspects. Furthermore, certain aspects of the present invention may take the form of a computer program product on a computer-usable storage medium having computer readable program code means embodied in the medium. Any suitable computer readable medium may be utilized including, but not limited to, hard disks, CD-ROMs, optical storage devices, and magnetic storage devices.

Certain aspects of the present invention are described below with reference to flowchart illustrations of methods, apparatus (systems), and computer program products. It will be understood that each block of the flowchart illustrations, and combinations of blocks in the flowchart illustrations, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the flowchart block or blocks.

Computer program instructions may also be stored in a computer-readable memory that can direct a computer or other programmable data processing apparatus to function in a particular manner, such that the instructions stored in the computer-readable memory produce an article of manufacture including instruction means which implement the function specified in the flowchart block or blocks.

Computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions specified in the flowchart block or blocks.

1. Definitions.

"Cardiac ischemia" refers to a lack of or insufficient blood supply to an area of cardiac muscle. Cardiac ischemia usually occurs in the presence of arteriosclerotic occlusion of a single or a group of coronary arteries. Arteriosclerosis is a product of a lipid deposition process resulting in fibro-fatty accumulations, or plaques, which grow on the internal walls of coronary arteries. Such an occlusion compromises blood flow through the artery, which reduction then impairs oxygen supply to the surrounding tissues during increased physiological need—for instance, during increased exercise loads. In the later stages of cardiac ischemia (e.g., significant coronary artery occlusion), the blood supply may be insufficient even while the cardiac muscle is at rest. However, in its earlier stages such ischemia is reversible in a manner analogous to how the cardiac muscle is restored to normal function when the oxygen supply to it returns to a normal physiological level. Thus, ischemia that may be detected by the present invention includes episodic, chronic and acute ischemia.

"Exercise" as used herein refers to voluntary skeletal muscle activity of a subject that increases heart rate above that found at a sustained stationary resting state. Examples of exercise include, but are not limited to, cycling, rowing, weight-lifting, walking, running, stair-stepping, etc., which may be implemented on a stationary device such as a treadmill or in a non-stationary environment.

"Exercise load" or "load level" refers to the relative strenuousness of a particular exercise, with greater loads or load levels for a given exercise producing a greater heart rate in a subject. For example, load may be increased in weight-lifting by increasing the amount of weight; load may be increased in walking or running by increasing the speed and/or increasing the slope or incline of the walking or running surface; etc.

"Gradually increasing" and "gradually decreasing" an exercise load refers to exercise in which the subject is caused to perform an exercise under a plurality of different sequentially increasing or sequentially decreasing loads. The number of steps in the sequence can be infinite so the terms gradually increasing and gradually decreasing loads include continuous load increase and decrease, respectively.

"Intervening rest", when used to refer to a stage following increased cardiac stimulation, refers to a stage of time initiated by a sufficiently abrupt decrease in heart stimulation (e.g., an abrupt decrease in exercise load) so that it evokes a clear sympatho-adrenal response. Thus, an intervening rest stage is characterized by a rapid sympatho-adrenal adjustment (as further described in Example 8 below), and the inclusion of an intervening rest stage precludes the use of a quasi-stationary exercise (or stimulation) protocol (as further described in Example 9 below).

"Hysteresis" refers to a lagging of the physiological effect when the external conditions are changed.

"Hysteresis curves" refer to a pair of curves in which one curve reflects the response of a system to a first sequence of conditions, such as gradually increasing heart rate, and the other curve reflects the response of a system to a second sequence of conditions, such as gradually decreasing heart rate. Here both sets of conditions are essentially the same—i.e., consist of the same (or approximately the same) steps—but are passed in different order in the course of time. A "hysteresis loop" refers to a loop formed by the two contiguous curves of the pair.

"Electrocardiogram" or "ECG" refers to a continuous or sequential record (or a set of such records) of a local electrical potential field obtained from one or more locations outside the cardiac muscle. This field is generated by the combined electrical activity (action potential generation) of multiple cardiac cells. The recording electrodes may be either subcutaneously implanted or may be temporarily attached to the surface of the skin of the subject, usually in the thoracic region. An ECG record typically includes the single-lead ECG signal that represents a potential difference between any two of the recording sites including the site with a zero or ground potential.

"Quasi-stationary conditions" refer to a gradual change in the external conditions and/or the physiological response it causes that occurs much slower than any corresponding adjustment due to sympathetic/parasympathetic and hormonal control. If the representative time of the external conditions variation is denoted by $\tau_{ext}$, and $\tau_{int}$ is a representative time of the fastest of the internal, sympathetic/parasympathetic and hormonal control, then "quasi-stationary conditions" indicates $\tau_{ext} \gg \tau_{int}$ (e.g., $\tau_{ext}$ is at least about five times greater than $\tau_{int}$) "An abrupt change" refers to an opposite situation corresponding to a sufficiently fast change in the external conditions as compared with the rate sympathetic/parasympathetic and hormonal control-that is, it requires that $\tau_{ext} \ll \tau_{int}$ (e.g., $\tau_{ext}$ is at least about five times less than $\tau_{int}$). In particular, "an abrupt stop" refers to a fast removal of the exercise load that occurs during time shorter than $\tau_{int}$ ~20 or 30 seconds (see FIG. 9 below and comments therein).

"QT- and RR-data set" refers to a record of the time course of an electrical signal comprising action potentials spreading through cardiac muscle. Any single lead ECG record incorporates a group of three consecutive sharp deflections usually called a QRS complex and generated by the propagation of the action potential's front through the ventricles. In contrast, the electrical recovery of ventricular tissue is seen on the ECG as a relatively small deflection known as the T wave. The time interval between the cardiac cycles (i.e., between the maxima of the consecutive R-waves) is called an RR-interval, while the action potential duration (i.e., the time between the beginning of a QRS complex and the end of the ensuing T-wave) is called a QT-interval. Alternative definitions of these intervals can be equivalently used in the framework of the present invention. For example, an RR-interval can be defined as the time between any two similar points, such as the similar inflection points, on two consecutive R-waves, or any other way to measure cardiac cycle length. A QT-interval can be defined as the time interval between the peak of the Q-wave and the peak of the T wave. It can also be defined as the time interval between the beginning (or the center) of the Q-wave and the end of the ensuing T-wave defined as the point on the time axis (the base line) at which it intersects with the linear extrapolation of the T-wave's falling branch and started from its inflection point, or any other way to measure action potential duration. An ordered set of such interval durations simultaneously with the time instants of their beginnings or ends which are accumulated on a beat to beat basis or on any given beat sampling rate basis form a corresponding QT- and RR-interval data set. Thus, a QT- and RR-interval data set will contain two QT-interval related sequences $\{T_{QT,1}, T_{QT,2}, \ldots, T_{QT,n},\}$ and $\{t_1, t_2, t_n\}$, and will also contain two RR-interval related sequences $\{T_{RR,1}, T_{RR,2}, \ldots T_{RR,n},\}$ and $\{t_1, t_2, \ldots, t_n\}$ (the sequence $\{t_1, t_2, \ldots, t_n\}$ may or may not exactly coincide with the similar sequence in the QT data set).

In the following definitions, C[a,b] shall denote a set of continuous functions j(t) on a segment [a,b]. $\{t_i\}$, i=1, 2, ..., N, denotes a set of points from [a,b], i.e. $\{t_i\} = \{t_i: a \leq t_i \leq b, i=1, 2, \ldots, N\}$ and $\{f(t_i)\}$, where $f \in C[a,b]$, denotes a set of values of the function f at the points $\{t_i\}$. In matrix operations the quantities $\tau = \{t_i\}$, $y = \{f(t_i)\}$, are treated as column vectors. $E_N$ shall denote a N-dimensional metric space with the metric $R_N(x,y)$, $x;y \in E_N$. ($R_N(x,y)$ is said to be a distance between points x and y.) A (total) variation $$\overset{b}{\underset{a}{V}}[F]$$

is defined for any absolutely continuous function F from C[a, b] as the integral (a Stieltjes integral)

$$\overset{b}{\underset{a}{V}}[F(t)] \equiv \int_a^b |dF(t)| = \int_a^b |F'(t)| dt. \quad (D.1)$$

For a function F monotonic on segment [a,b] its variation is simply |F(a)-F(b)|. If a function F(t) has alternating maxima and minima, then the total variation of F is the sum of its variations on the intervals of monotonicity. For example, if the points of minima and maxima are $x_1=a, x_2, x_3, \ldots x_k=b$ then $$\overset{b}{\underset{a}{V}}[F(t)] = \sum_{i=1}^{k-1} |F(x_i) - F(x_{i+1})|. \quad (D.2)$$

Fitting (Best Fitting):

Let $\tilde{C}[a,b]$ be a subset of C[a,b]. A continuous function f(t), $f \in \tilde{C}[a,b]$ is called the (best) fit (or the best fitting) function of class $\tilde{C}[a,b]$ with respect to metric $R_N$ to a data set $\{x_i, t_i\}$ (i=1, 2, ..., N) if $$R_N(\{f(t_i)\}, \{x_i\}) = \min_{f \in \tilde{C}[a,b]} \quad (D.3)$$

The minimum value of $R_N$ is then called the error of the fit. The functions f(t) from $\tilde{C}[a,b]$ will be called trial functions.

In most cases $E_N$ is implied to be an Euclidean space with an Euclidean metric. The error $R_N$ then becomes the familiar mean-root-square error. The fit is performed on a subset $\tilde{C}[a,b]$ since it usually implies a specific parametrization of the trial functions and/or such constrains as the requirements that the trial functions pass through a given point and/or have a given value of the slope at a given point.

A Smoother Function (Comparison of Smoothness):

Let f(t) and g(t) be functions from C[a,b] that have absolutely continuous derivatives on this segment. The function f(t) is smoother than the function g(t) if $$\overset{b}{\underset{a}{V}}[f(t)] \leq \overset{b}{\underset{a}{V}}[g(t)], \quad (D.4)$$

and $$\overset{b}{\underset{a}{V}}[f'(t)] \leq \overset{b}{\underset{a}{V}}[g'(t)], \tag{D.5}$$

where the prime denotes a time derivative, and a strict inequality holds in at least one of relations (D.4) and (D.5).

A Smoother Set:

A set $\{x_i, t_i\}$ (i=1, 2, ..., N) is smoother than the set $\{x'_j, t'_j\}$ (j=1, 2, ..., $N_0$) if the former can be fit with a smoother function f(t) of the same class within the same or smaller error than the latter.

Smoothing of a Data Set:

A (linear) transformation of a data set $(x,t) \equiv \{x_i, t_i\}$ (i=1, 2, ..., $N_0$) into another set $(y,\tau) \equiv \{y_j, \tau_j\}$ (j=1, 2, ..., $N_1$) of the form $$y = A \cdot x, \quad \tau = B \cdot t, \tag{D.6}$$

where A and B are $N_1 \times N_0$ matrices, is called a smoothing if the latter set is smoother than the former. One can refer to $\{y_j, \tau_j\}$ as a smoothed set A Measure of a Closed Domain:

Let $\Omega$ be a singly connected domain on the plane $(\tau, T)$ with the boundary formed by a simple (i.e., without self-intersections) continuous curve. A measure M of such a domain $\Omega$ on the plane $(\tau, T)$ is defined as the Riemann integral $$M = \iint_{\Omega} \rho(\tau, T) d\tau dT \tag{D.7}$$

where $\tau(\tau, T)$ is a nonnegative (weight) function on $\Omega$.

Note that when $\rho(\tau, T) = 1$ the measure M of the domain coincides with its area, A; when $\tau(\tau, T) = 1/\tau^2$, the measure, M, has the meaning of the area, A' of the domain $\Omega'$ on the transformed plane (f,T), where $f = 1/\tau$ can be understood as the heart rate since the quantity $\tau$ has the meaning of RR-interval. [The domain $\Omega'$ is the image of domain $\Omega$ under the mapping $(\tau, T) \to (1/\tau, T)$.]

2. Dispersion/Restitution Curves.

FIG. 1 illustrates the correspondence between the temporal phases of the periodic action potential (AP, upper graph, 20) generated inside cardiac muscle and summed up over its entire volume and the electrical signal produced on the body surface and recorded as an electrocardiogram (ECG, lower graph, 21). The figure depicts two regular cardiac cycles. During the upstroke of the action potential the QRS-complex is formed. It consists of three waves, Q, R, and S, which are marked on the lower panel. The recovery stage of the action potential is characterized by its fall off on the AP plot and by the T-wave on the ECG plot. One can see that the action potential duration is well represented by the time between Q and T waves and is conventionally defined as the QT interval, measured from the beginning of the Q wave to the end of the following T wave. The time between consecutive R-waves (RR interval) represents the duration of a cardiac cycle, while its reciprocal value represents the corresponding instantaneous heart rate.

Figure 2:
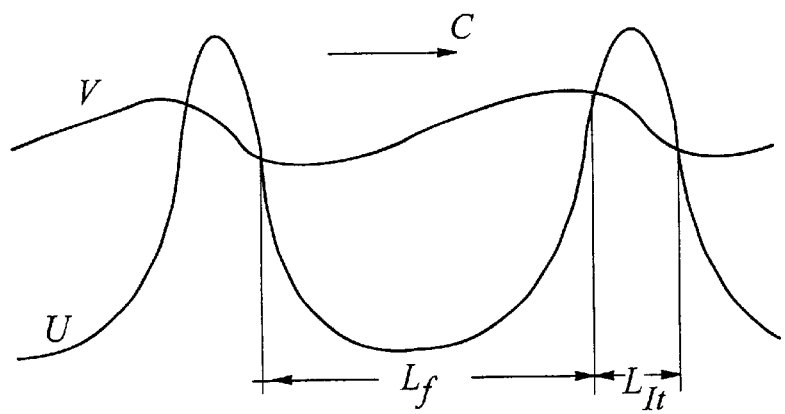
FIG. 2A depicts the equations used in a simplified mathematical model of periodic excitation.
FIG. 2B depicts a periodic excitation wave (action potential, u, and instantaneous threshold, v, generated by computer using a simplified mathematical model, the equations of which are set forth in FIG. 2A.
FIG. 2C depicts a family of four composite dispersion-restitution curves corresponding to four values of the medium excitation threshold.
Figure 2:
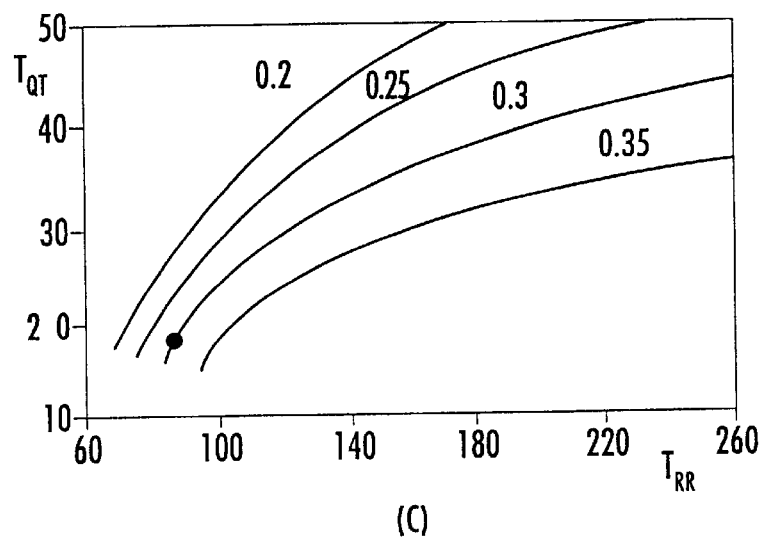

FIG. 2 illustrates major aspects of the process of propagation of a periodic action potential through cardiac tissue and the formation of a corresponding composite dispersion-restitution curve. The tissue can be considered as a continuous medium and the propagation process as a repetition at each medium point of the consecutive phases of excitation and recovery. The former phase is characterized by a fast growth of the local membrane potential (depolarization), and the latter by its return to a negative resting value (repolarization). The excitation phase involves a very fast (~0.1 ms) decrease in the excitation threshold and the following development of a fast inward sodium current that causes the upstroke of the action potential (~1 ms). Next, during an intermediate plateau phase (~200 ms) sodium current is inactivated; calcium and potassium currents are developing while the membrane is temporarily unexcitable (i.e., the threshold is high). During the next recovery phase (~100 ms), a potassium current repolarizes the membrane so it again becomes excitable (the excitation threshold is lowered).

The complicated description of a multitude of ionic currents involved in the process can be circumvented if one treats the process directly in terms of the local membrane potential, u, and a local excitation threshold, v. Such a mathematical description referred to as the CSC model, was developed by Chernyak, Starobin, & Cohen (*Phys. Rev. Lett.*, 80, pp.5675–5678, 1998) and is presented as a set of two Reaction-Diffusion (RD) equations in panel A. The left-hand side of the first equation describes local accumulation of the electric charge on the membrane, the first term in the right-hand side describes Ohmic coupling between neighboring points of the medium, and the term i(u,v) represents the transmembrane current as a function of the membrane potential and the varying excitation threshold (e is a small constant, the ratio of the slow recovery rate to the fast excitation rate). A periodic solution (a wave-train) can be found analytically for some particular functions i(u,v) and g(u,v). The wave-train shown in panel B has been calculated for $g(u,v) = \zeta u + v_r - v$, where $\zeta$ and $v_r$ are appropriately chosen constants ($v_r$ has the meaning of the initial excitation threshold and is the main determinant of the medium excitability). The function i(u,v) was chosen to consist of two linear pieces, one for the sub-threshold region, u<v, and one for supra-threshold region, u>v. That is $i(u,v) = \lambda_r u$ when $u \leq v$, and $i(u,v) = \lambda_{ex}(u - u_{ex})$ when u>v, where $\lambda_r$ and $\lambda_{ex}$ are membrane chord conductances in the resting (u=0) and excited (u=$u_{ex}$) states, respectively. The resting state u=0 is taken as the origin of the potential scale. We used such units that $\lambda_{ex} = 1$ and $u_{ex} = 1$. (For details see Chernyak & Starobin, *Critical Reviews in Biomed. Eng.* 27, 359–414 (1999)).

A medium with higher excitability, corresponding to the tissue with better conduction, gives rise to a faster, more robust action potential with a longer Action Potential Duration (APD). This condition also means that a longer-lasting excitation propagates faster. Similarly, a wave train with a higher frequency propagates slower since the medium has less time to recover from the preceding excitation and thus has a lower effective excitability. These are quite generic features that are incorporated in the CSC model. In physics, the relation between the wave's speed, c, and its frequency, f, or its period, T=1/f is called a dispersion relation. In the CSC model the dispersion relation can be obtained in an explicit form $T = F_T(c)$, where $F_T$ is a known function of c and the medium parameters. The CSC model also allows us to find a relation between the propagation speed and the APD, $T_{AP}$, in the explicit form $T_{AP} = F_{AP}(c)$, which represents the restitution properties of the medium. In the medical literature, the restitution curve is $T_{AP}$ versus diastolic interval $T_{DI}$, which differently makes a quite similar physical statement. One can consider a pair of dispersion and restitution relations $\{T = F_T(c), T_{AP} = F_{AP}(c)\}$ as a parametric representation of a single curve on the $(T, T_{AP})$-plane as shown in panel C (FIG. 2). Such a curve (relation) shall be referred to as a composite dispersion-restitution curve (relation) and can be directly obtained from an experimental ECG recording by determining the QT-RR interval data set and plotting $T_{QT}$ versus $T_{RR}$. A condition that the experimental $\{T_{QT}, T_{RR}\}$ data set indeed represents the composite dispersion-restitution relation is the requirement that the data are collected under quasi-stationary conditions. Understanding this fact is a key discovery for the present invention.

3. Testing Methods.

The methods of the present invention are primarily intended for the testing of human subjects. Virtually any human subject can be tested by the methods of the present invention, including male, female, juvenile, adolescent, adult, and geriatric subjects. The methods may be carried out as an initial screening test on subjects for which no substantial previous history or record is available, or may be carried out on a repeated basis on the same subject (particularly where a comparative quantitative indicium of an individual's cardiac health over time is desired) to assess the effect or influence of intervening events and/or intervening therapy on that subject between testing sessions.

As noted above, the method of the present invention generally comprises (a) collecting a first QT- and RR-interval data set from said subject during a stage of gradually increasing heart rate; (b) collecting a second QT- and RR-interval data set from said subject during a stage of gradually decreasing heart rate; (c) comparing said first QT- and RR-interval data set to said second QT- and RR-interval data set to determine the difference between said data sets; and (d) generating from said comparison of step (c) a measure of cardiac ischemia in the subject. A greater difference between the first and second data sets indicates greater cardiac ischemia and lesser cardiac or cardiovascular health in that subject.

The stages of gradually increasing and gradually decreasing heart rate are carried out in a manner that maintains during both periods essentially or substantially the same stimulation of the heart by the peripheral nervous and hormonal control systems, so that it is the effect of cardiac ischemia rather than that of the external control which is measured by means of the present invention. This methodology can be carried out by a variety of techniques, with the technique of conducting two consecutive stages of gradually increasing and gradually decreasing exercise loads (or average heart rates) being currently preferred.

The stage of gradually increasing exercise load (or increased average heart rate and the stage of gradually decreasing exercise load (or decreased average heart rate) may be the same in duration or may be different in duration. In general, each stage is at least 3, 5, 8, or 10 minutes or more in duration. Together, the duration of the two stages may be from about 6, 10, 16 or 20 minutes in duration to about 30, 40, or 60 minutes in duration or more. The two stages are preferably carried out sequentially in time-that is, with one stage following after the other substantially immediately, without an intervening rest stage. In the alternative, the two stages may be carried out separately in time, with an intervening "plateau" stage (e.g., of from 1 to 5 minutes) during which cardiac stimulation or exercise load is held substantially constant, before the stage of decreasing load is initiated.

The exercise protocol may include the same or different sets of load steps during the stages of increasing or decreasing heart rates. For example, the peak load in each stage may be the same or different, and the minimum load in each stage may be the same or different. In general, each stage consists of at least two or three different load levels, in ascending or descending order depending upon the stage. Relatively high load levels, which result in relatively high heart rates, can be used but are not essential. An advantage of the present invention is that its sensitivity allows both exercise procedures to be carried out at relatively low load levels that do not unduly increase the pulse rate of the subject. For example, the method may be carried out so that the heart rate of the subject during either the ascending or descending stage (or both) does not exceed about 140, 120, or even 100 beats per minute, depending upon the condition of the subject. Of course, data collected at heart rates above 100, 120, or 140 beats per minute may also be utilized if desired, again depending upon the condition of the subject.

For example, for an athletic or trained subject, for the first or ascending stage, a first load level may be selected to require a power output of 60 to 100 or 150 watts by the subject; an intermediate load level may be selected to require a power output of 100 to 150 or 200 watts by the subject; and a third load level may be selected to require a power output of 200 to 300 or 450 watts or more by the subject. For the second or descending stage, a first load level may be selected to require a power output of 200 to 300 or 450 watts or more by the subject; an intermediate or second load level may be selected to require a power output of 100 to 150 or 200 watts by the subject; and a third load level may be selected to require a power output of 60 to 100 or 150 watts by the subject. Additional load levels may be included before, after, or between all of the foregoing load levels as desired, and adjustment between load levels can be carried out in any suitable manner, including step-wise or continuously.

In a further example, for an average subject or a subject with a history of cardiovascular disease, for the first or ascending stage, a first load level may be selected to require a power output of 40 to 75 or 100 watts by the subject; an intermediate load level may be selected to require a power output of 75 to 100 or 150 watts by the subject; and a third load level may be selected to require a power output of 125 to 200 or 300 watts or more by the subject. For the second or descending stage, a first load level may be selected to require a power output of 125 to 200 or 300 watts or more by the subject; an intermediate or second load level may be selected to require a power output of 75 to 100 or 150 watts by the subject; and a third load level may be selected to require a power output of 40 to 75 or 100 watts by the subject. As before, additional load levels may be included before, after, or between all of the foregoing load levels as desired, and adjustment between load levels can be carried out in any suitable manner, including step-wise or continuously.

The heart rate may be gradually increased and gradually decreased by subjecting the patient to a predetermined schedule of stimulation. For example, the patient may be subjected to a gradually increasing exercise load and gradually decreasing exercise load, or gradually increasing electrical or pharmacological stimulation and gradually decreasing electrical or pharmacological stimulation, according to a predetermined program or schedule. Such a predetermined schedule is without feedback of actual heart rate from the patient. In the alternative, the heart rate of the patient may be gradually increased and gradually decreased in response to actual heart rate data collected from concurrent monitoring of said patient. Such a system is a feedback system. For example, the heart rate of the patient may be monitored during the test and the exercise load (speed and/or incline, in the case of a treadmill) can be adjusted so that the heart rate varies in a prescribed way during both stages of the test.

The monitoring and control of the load can be accomplished by a computer or other control system using a simple control program and an output panel connected to the control system and to the exercise device that generates an analog signal to the exercise device. One advantage of such a feedback system is that (if desired) the control system can insure that the heart rate increases substantially linearly during the first stage and decreases substantially linearly during the second stage.

The generating step (d) may be carried out by any suitable means, such as by generating curves from the data sets (with or without actually displaying the curves), and then (i) directly or indirectly evaluating a measure (e.g., as defined in the integral theory) of the domain (e.g., area) between the hysteresis curves, a greater measure indicating greater cardiac ischemia in said subject, (ii) directly or indirectly comparing the shapes (e.g., slopes or derivatives thereof) of the curves, with a greater difference in shape indicating greater cardiac ischemia in the subject; or (iii) combinations of (i) and (ii). Specific examples are given in Example 4 below.

The method of the invention may further comprise the steps of (e) comparing the measure of cardiac ischemia during exercise to at least one reference value (e.g., a mean, median or mode for the quantitative indicia from a population or subpopulation of individuals) and then (f) generating from the comparison of step (e) at least one quantitative indicium of cardiovascular health for said subject. Any such quantitative indicium may be generated on a one-time basis (e.g., for assessing the likelihood that the subject is at risk to experience a future ischemia-related cardiac incident such as myocardial infarction or ventricular tachycardia), or may be generated to monitor the progress of the subject over time, either in response to a particular prescribed cardiovascular therapy, or simply as an ongoing monitoring of the physical condition of the subject for improvement or decline (again, specific examples are given in Example 4 below). In such a case, steps (a) through q) above are repeated on at least one separate occasion to assess the efficacy of the cardiovascular therapy or the progress of the subject. A decrease in the difference between said data sets from before said therapy to after said therapy, or over time, indicates an improvement in cardiac health in said subject from said cardiovascular therapy. Any suitable cardiovascular therapy can be administered, including but not limited to, aerobic exercise, muscle strength building, change in diet, nutritional supplement, weight loss, smoking cessation, stress reduction, pharmaceutical treatment (including gene therapy), surgical treatment (including both open heart and closed heart procedures such as bypass, balloon angioplasty, catheter ablation, etc.) and combinations thereof.

The therapy or therapeutic intervention may be one that is approved or one that is experimental. In the latter case, the present invention may be implemented in the context of a clinical trial of the experimental therapy, with testing being carried out before and after therapy (and/or during therapy) as an aid in determining the efficacy of the proposed therapy.

4. Testing Apparatus.

Figure 3:
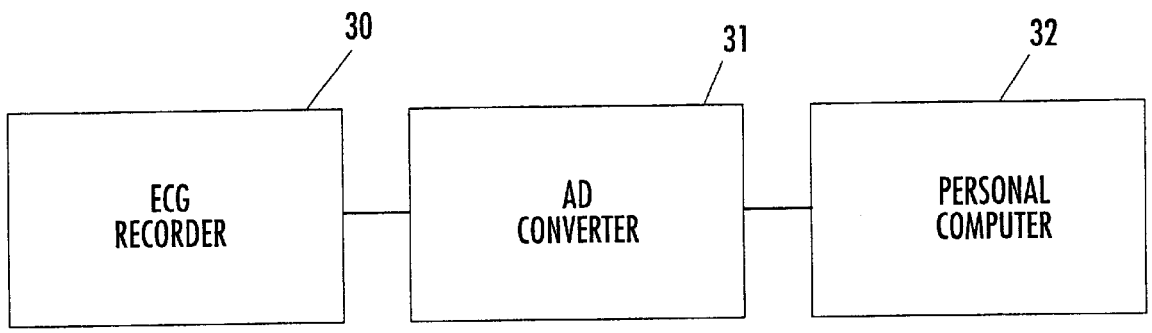
FIG. 3 is a block diagram of an apparatus for carrying out the present method.

FIG. 3 provides an example of the apparatus for data acquisition, processing and analysis by the present invention. Electrocardiograms are recorded by an ECG recorder 30, via electrical leads placed on a subject's body. The ECG recorder may be, for example, a standard multi-lead Holter recorder or any other appropriate recorder. The analog/digital converter 31 digitizes the signals recorded by the ECG recorder and transfers them to a personal computer 32, or other computer or central processing unit, through a standard external input/output port. The digitized ECG data can then be processed by standard computer-based waveform analyzer software. Composite dispersion-restitution curves and a cardiac or cardiovascular health indicium or other quantitative measure of the presence, absence or degree of cardiac ischemia can then be calculated automatically in the computer through a program (e.g., Basic, Fortran, C++, etc.) implemented therein as software, hardware, or both hardware and software.

Figure 4A:
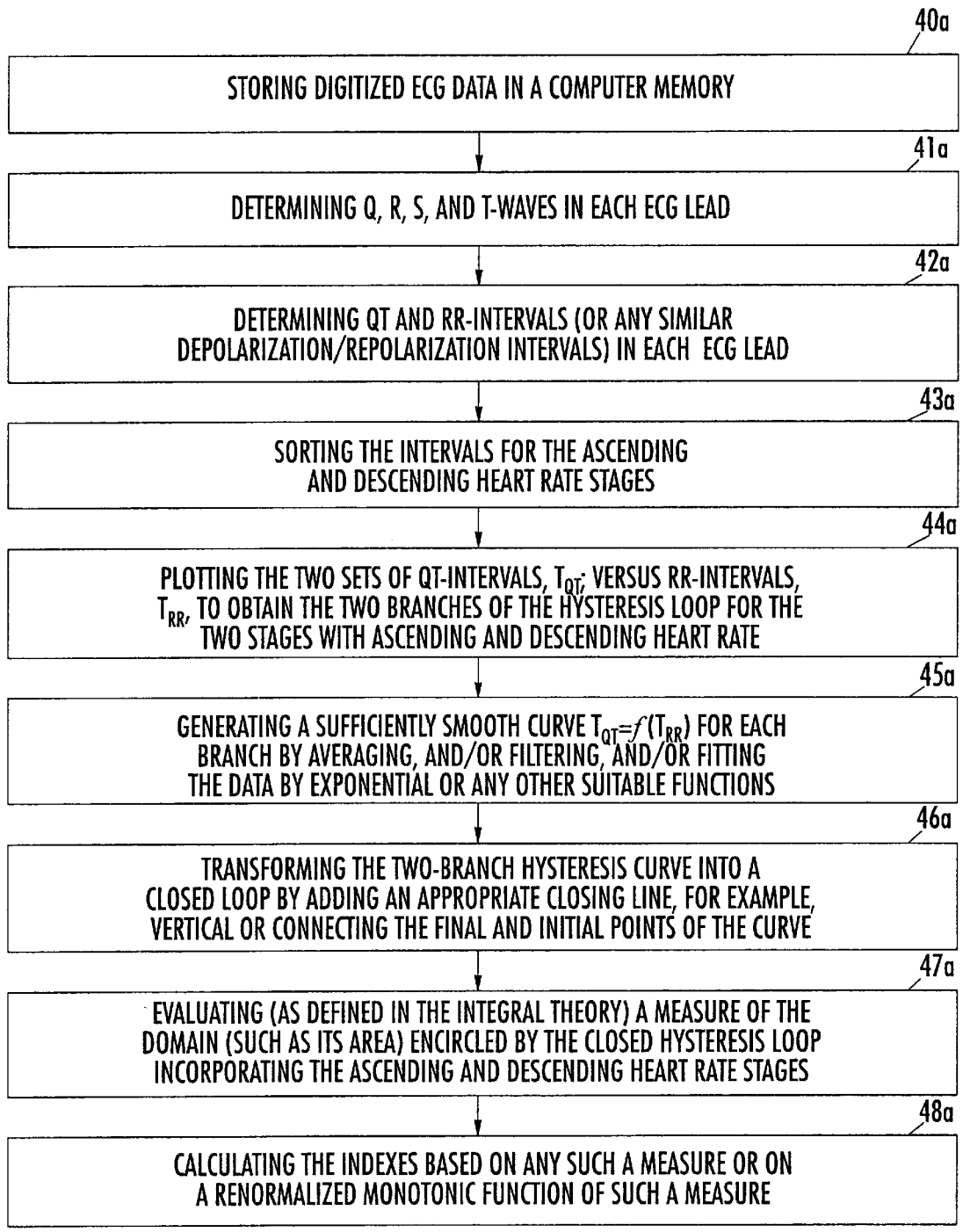
FIG. 4A is a block diagram of the processing steps for data acquisition and analysis of the present invention.
Figure 4B:
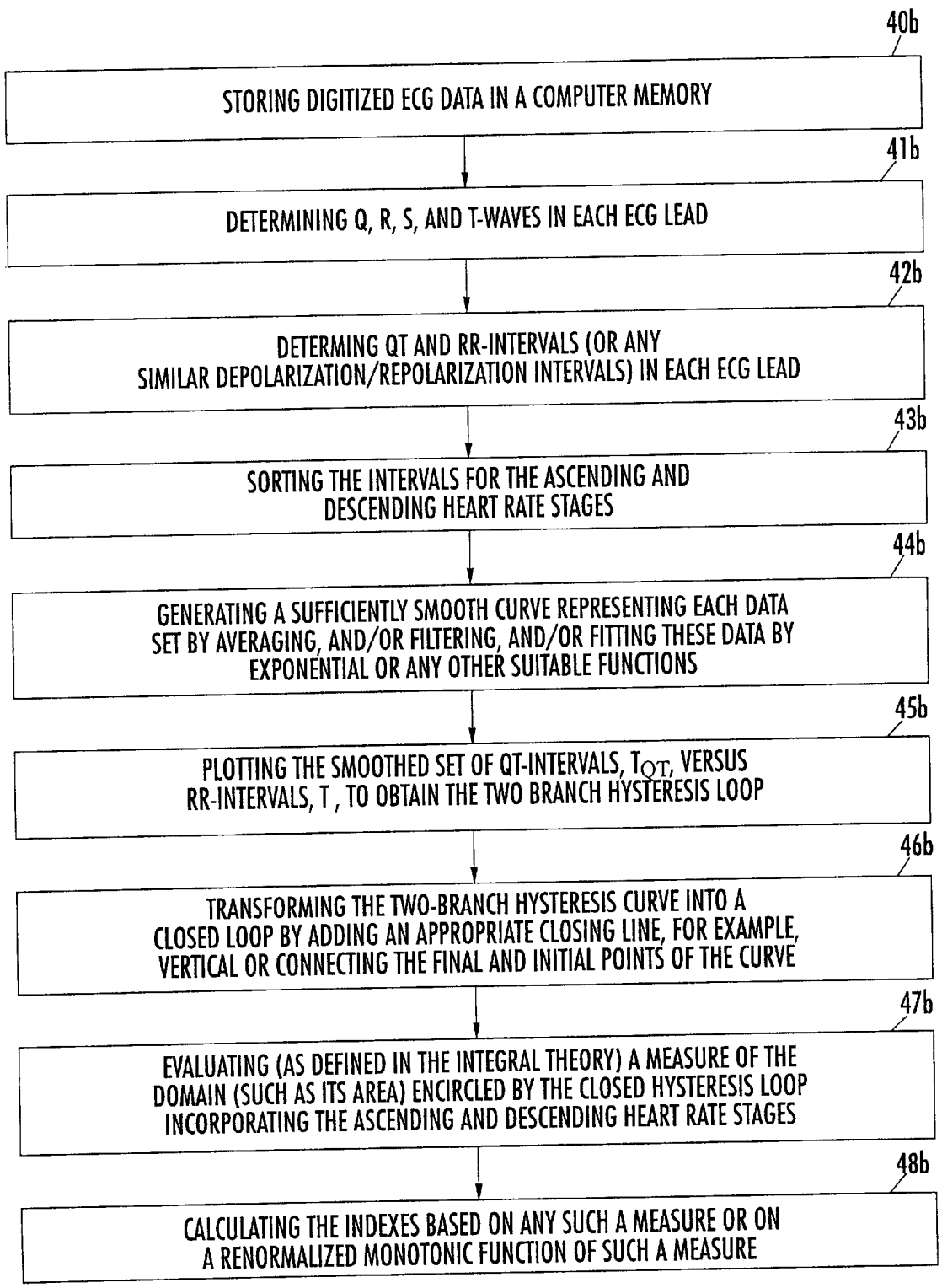
FIG. 4B is an alternative block diagram of the processing steps for data acquisition and analysis of the present invention.

FIG. 4A and FIG. 4B illustrate the major steps of digitized data processing in order to generate an analysis of a QT-RR data set collected from a subject during there-and-back quasi-stationary changes in physiological conditions. The first four steps in FIG. 4A and FIG. 4B are substantially the same. The digitized data collected from a multi-lead recorder are stored in a computer memory for each lead as a data array 40a, 40b. The size of each data array is determined by the durations of the ascending and descending heart rate stages and a sampling rate used by the waveform analyzer, which processes an incoming digitized ECG signal. The waveform analyzer software first detects major characteristic waves (Q, R, S and T waves) of the ECG signal in each particular lead 41a, 41b. Then in each ECG lead it determines the time intervals between consecutive R waves and the beginning of Q and the end of T waves 42a, 42b. Using these reference points it calculates heart rate and RR- and QT-intervals. Then, the application part of the software sorts the intervals for the ascending and descending heart rate stages 43a, 43b. The next two steps can be made in one of the two alternative ways shown in FIGS. 4A and 4B, respectively. The fifth step as shown in FIG. 4A consists of displaying by the application part of software QT-intervals versus RR-intervals 44a, separately for the ascending and descending heart rate stages effected by there-and-back gradual changes in physiological conditions such as exercise, pharmacological/electrical stimulation, etc. The same part of the software performs the next step 45a, which is smoothing, filtering or data fitting, using exponential or any other suitable functions, in order to obtain a sufficiently smooth curve $T_{QT}F(T_{RR})$ for each stage. An alternative for the last two steps shown in FIG. 4B requires that the application part of the software first averages, and/or filters and/or fits, using exponential or any other suitable functions, the QT intervals as functions of time for both stages and similarly processes the RR-interval data set to produce two sufficiently smooth curves $T_{QT}=F_{QT}(t)$ and $T_{RR}=F_{RR}(t)$, each including the ascending and descending heart rate branches 44b. At the next step 45b the application part of the software uses this parametric representation to eliminate time and generate and plot a sufficiently smooth hysteresis loop $T_{QT}=F(T_{RR})$. The following steps shown in FIGS. 4A and FIG. 4B are again substantially the same. The next step 46a, 46b performed by the application part of the software can be graphically presented as closing the two branch hysteresis loop with an appropriate interconnecting or partially connecting line, such as a vertical straight line or a line connecting the initial and final points, in order to produce a closed hysteresis loop on the $(T_{QT}, T_{RR})$-plane. At the next step 47a, 47b the application software evaluates for each ECG lead an appropriate measure of the domain inside the closed hysteresis loop. A measure, as defined in mathematical integral theory, is a generalization of the concept of an area and may include appropriate weight functions increasing or decreasing the contribution of different portions of the domain into said measure. The final step 48a, 48b of the data processing for each ECG lead is that the application software calculates indexes by appropriately renormalizing the said measure or any monotonous functions of said measure. The measure itself along with the indexes may reflect both the severity of the exercise-induced ischemia, as well as a predisposition to local ischemia that can be reflected in some particularities of the shape of the measured composite dispersion-restitution curves. The results of all above-mentioned signal processing steps may be used to quantitatively assess cardiac ischemia and, as a simultaneous option, cardiovascular system health of a particular individual under test.

Instead of using the ($T_{QT}$, $T_{RR}$)-plane a similar data processing procedure can equivalently be performed on any plane obtained by a non-degenerate transformation of the ($T_{QT}$,$T_{RR}$)-plane, such as ($T_{QT}F_{RR}$) where $f_{RR}=1/T_{RR}$ is the heart rate or the like. Such a transformation can be partly or fully incorporated in the appropriate definition of the said measure.

5. RR-Interval Monitoring with Blood Pressure and/or Pulse Signals.

A quasi-stationary RR data set can be collected non-invasively not only via measurements of a cardiac surface ECG but also by monitoring a blood pressure and/or pulse signals. In these cases, instead of the ECG recorder, a system for assessing cardiac ischemia may comprise pulse and/or blood pressure monitors, as discussed below.

A pulse monitor or pulse meter may be suitable device, including but not limited to opto-electronic and phono or audio transducers attached to different parts of a subject's body (for example, to a finger as in finger plethysmography), which device measures a heart rate or pulse (HR). Preferably the device then computes RR-intervals equal to 1/HR and stores these data in a computer memory in order to provide further RR-interval computational analysis as described herein.

A blood pressure monitor (e.g., a sphygmomanometer) can be any suitable device, including but not limited to a cuff, a stethoscope, or an automatic pressure registering system with a digital data storage module. Many such monitoring devices are applicable even for home use and typically contain all of the modules in one unit. An automatic cuff inflation monitor may also be included in the unit. Most units are portable and have a D-ring cuff for one-handed application. The cuff usually fits around the upper arm or the wrist. These units provide personalized cuff inflation and deflation. They automatically adjust to changes in subject's blood pressure. Blood pressure monitoring with simultaneous measurement of the HR is convenient, easy to do and takes less than a minute per measurement. As in the case above, the RR-intervals are equal to 1/HR. Such apparatus may be easily incorporated into a method and apparatus of the present invention with suitable interfaces, in accordance with known techniques.

The options described above may be used separately or in parallel, including in parallel with ECG data, depending on experimental needs. Pulse meter ischemia assessment is expected to be more accurate than blood pressure monitoring since an RR sampling frequency (frequency of HR measurements) for a pulse meter is at least an order of magnitude higher (10 to 1 data point) than in the case of blood pressure monitoring by an automatic sphygmomanometer.

The present invention is explained in greater detail in the non-limiting examples set forth below.

EXAMPLE 1

Testing Apparatus

A testing apparatus consistent with FIG. 3 was assembled. The electrocardiograms are recorded by an RZ152PM12 Digital ECG Holter Recorder (ROZINN ELECTRONICS, INC.; 71-22 Myrtle Av., Glendale, N.Y., USA 11385-7254), via 12 electrical leads with Lead-Lok Holter/Stress Test Electrodes LL510 (LEAD-LOK, INC.; 500 Airport Way, P.O. Box L, Sandpoint, Id., USA 83864) placed on a subject's body in accordance with the manufacturer's instructions. Digital ECG data are transferred to a personal computer (Dell Dimension XPS T500 MHz/Windows 98) using a 40 MB flash card (RZFC40) with a PC 700 flash card reader, both from Rozinn Electronics, Inc. Holter for Windows (4.0.25) waveform analysis software is installed in the computer, which is used to process data by a standard computer based waveform analyzer software. Composite dispersion-restitution curves and an indicium that provides a quantitative characteristic of the extent of cardiac ischemia are then calculated manually or automatically in the computer through a program implemented in Fortran 90.

Experimental data were collected during an exercise protocol programmed in a Landice L7 Executive Treadmill (Landice Treadmills; 111 Canfield Av., Randolph, N.J. 07869). The programmed protocol included 20 step-wise intervals of a constant exercise load from 48 seconds to 1.5 minutes each in duration. Altogether these intervals formed two equal-in-duration gradually increasing and gradually decreasing exercise load stages, with total duration varying from 16 to 30 minutes. For each stage a treadmill belt speed and elevation varied there-and-back, depending on the subject's age and health conditions, from 1.5 miles per hour to 5.5 miles per hour and from one to ten degrees of treadmill elevation, respectively.

EXAMPLES 2–6

Human Hysteresis Curve Studies

These examples illustrate quasi-stationary ischemia-induced QT-RR interval hystereses in a variety of different human subjects. These data demonstrate a high sensitivity and the high resolution of the method.

EXAMPLES 2–3

Hysteresis Curves in Healthy Male Subjects of Different Ages

Figure 5:
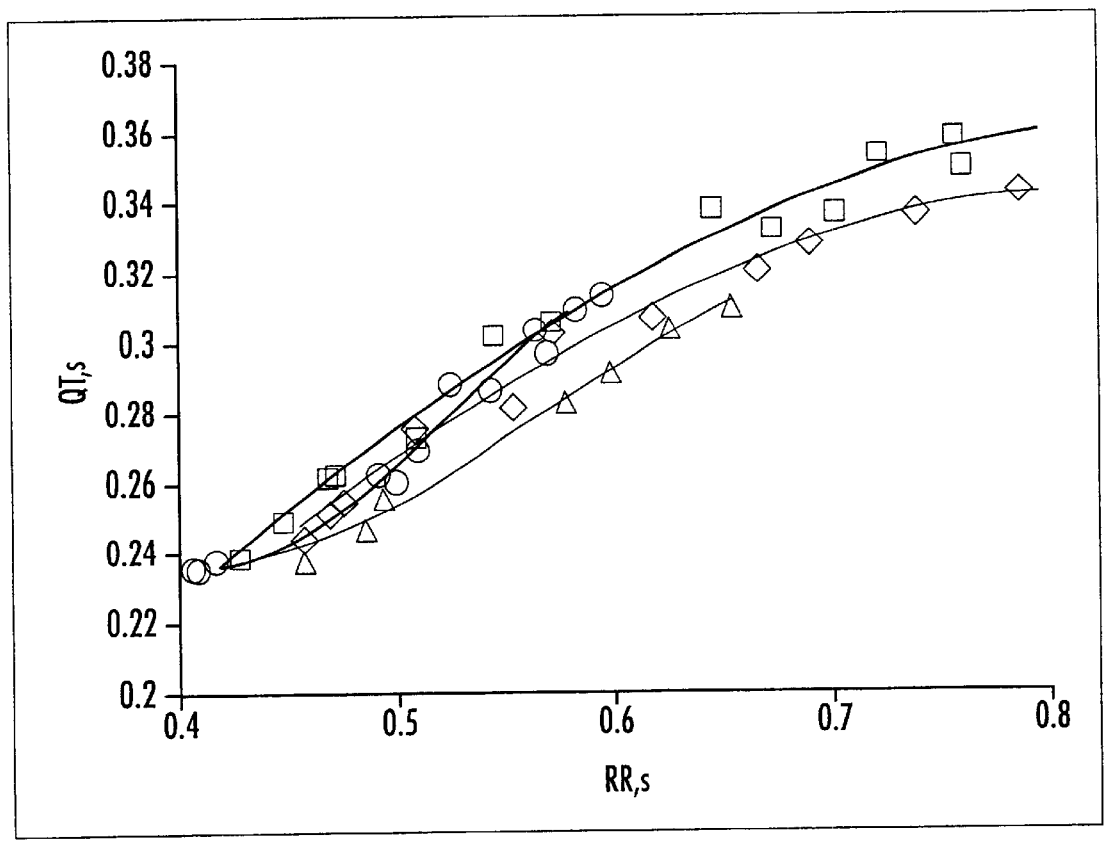
FIG. 5 illustrates experimental QT-interval versus RR-interval hysteresis loops for two healthy male (23 year old, thick line and 47 year old, thin line) subjects plotted on the composite dispersion-restitution curve plane.

These examples were carried out on two male subjects with an apparatus and procedure as described in Example 1 above. Referring to FIG. 5, one can readily see a significant difference in areas of hystereses between two generally healthy male subjects of different ages. These subjects (23 and 47 years old) exercised on a treadmill according to a quasi-stationary 30-minute protocol with gradually increasing and gradually decreasing exercise load. Here squares and circles (thick line) indicate a hysteresis loop for the 23 year old subject, and diamonds and triangles (thin line) correspond to a larger loop for the 47 year old subject. Fitting curves are obtained using the third-order polynomial functions. A beat sampling rate with which a waveform analyzer determines QT and RR intervals is equal to one sample per minute. Neither of the subjects had a conventional ischemia-induced depression of the ECG-ST segments. However, the method of the present invention allows one to observe ischemia-induced hystereses that provide a satisfactory resolution within a conventionally sub-threshold range of ischemic events and allows one to quantitatively differentiate between the hystereses of the two subjects.

EXAMPLES 4–5

Figure 6:
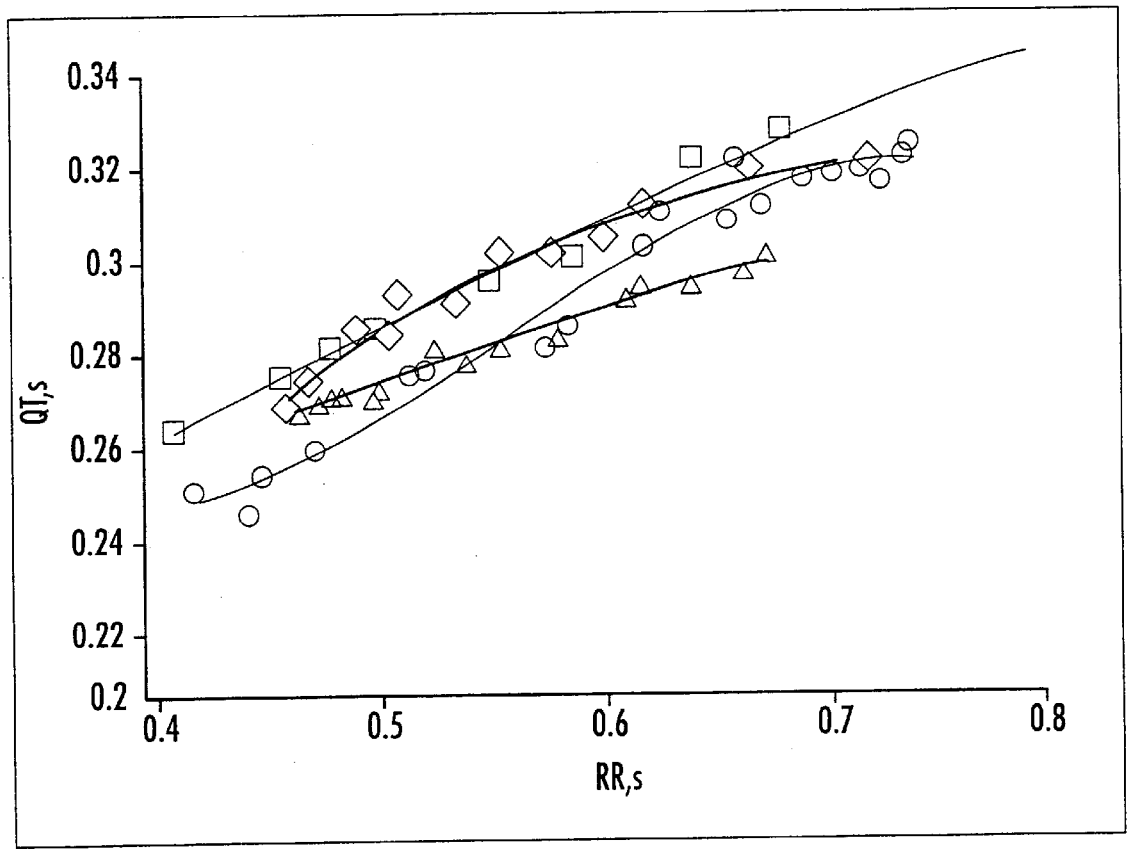
FIG. 6 provides examples of the QT-RR interval hysteresis for two male subjects, one with a conventional ECG ST-segment depression (thin line) and one with a history of a myocardial infarction 12 years prior to the test (thick line). The generation of the curves is explained in greater detail in the specification below.

Hysteresis Curves for Subjects with ST Segment Depression or Prior Cardiac Infarction These examples were carried out on two 55-year-old male subjects with an apparatus and procedure as described in Example 1 above. FIG. 6 illustrates quasi-stationary QT-RR interval hystereses for the male subjects. The curves fitted to the squares and empty circles relate to the first individual and illustrate a case of cardiac ischemia also detectable by the conventional ECG-ST segment depression technique. The curves fitted to the diamonds and triangles relate to the other subject, an individual who previously had experienced a myocardial infarction. These subjects exercised on a treadmill according to a quasi-stationary 20-minute protocol with a gradually increasing and gradually decreasing exercise load. Fitting curves are obtained using third-order polynomial functions. These cases demonstrate that the method of the present invention allows one to resolve and quantitatively characterize the difference between (1) levels of ischemia that can be detected by the conventional ST depression method, and (2) low levels of ischemia (illustrated in FIG. 5) that are subthreshold for the conventional method and therefore undetectable by it. The levels of exercise-induced ischemia reported in FIG. 5 are significantly lower than those shown in FIG. 6. This fact illustrates insufficient resolution of a conventional ST depression method in comparison with the method of the present invention.

EXAMPLE 6

Figure 7:
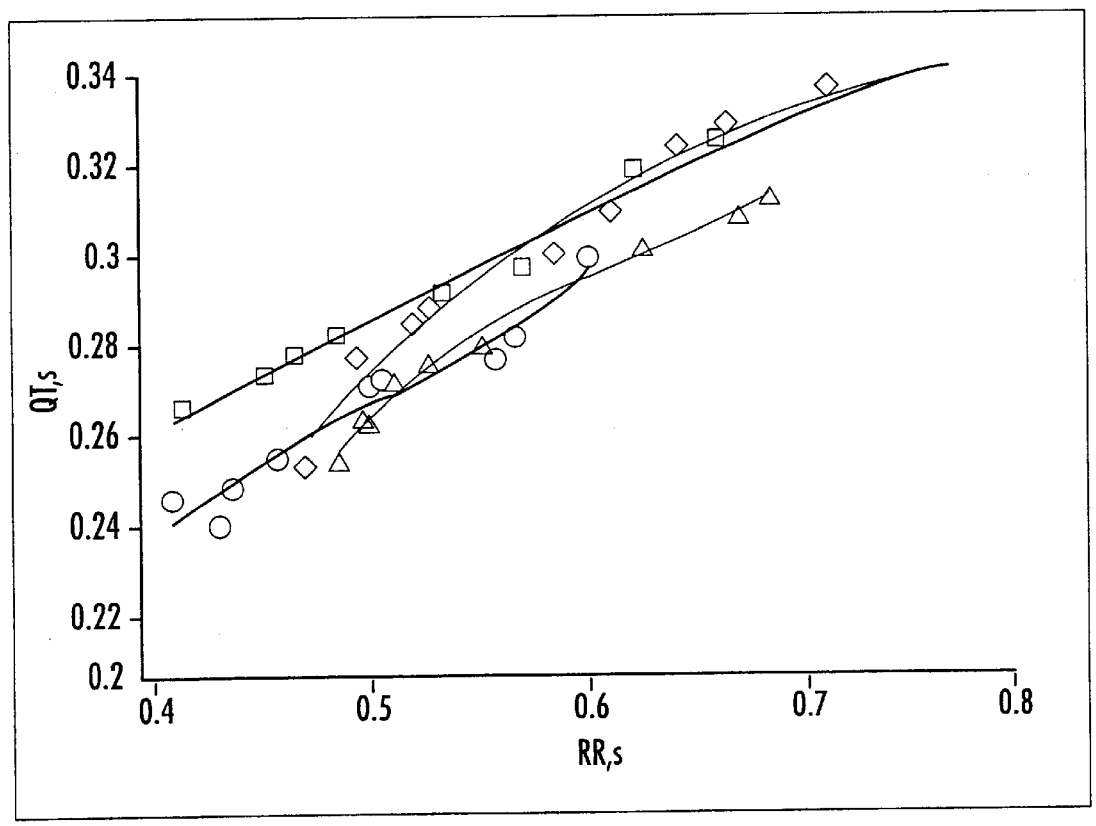
FIG. 7 illustrates sensitivity of the present invention and shows two QT-RR interval hysteresis loops for a male subject, the first one (thick lines) corresponds to the initial test during which an ST-segment depression on a conventional ECG was observed, and the second one shown by thin lines measured after a period of regular exercise.

Hysteresis Curves in the Same Subject Before and After a Regular Exercise Regimen This example was carried out with an apparatus and procedure as described in Example 1 above. FIG. 7 provides examples of quasi-stationary hystereses for a 55 year-old male subject before and after he engaged in a practice of regular aerobic exercise. Both experiments were performed according to the same quasi-stationary 20-minute protocol with a gradually increasing and gradually decreasing exercise load. Fitting curves are obtained using third-order polynomial functions. The first test shows a pronounced exercise-induced cardiac ischemic event developed near the peak level of exercise load, detected by both the method of the present invention and a conventional ECG-ST depression method. The maximum heart rate reached during the first test (before a regular exercise regimen was undertaken) was equal to 146. After a course of regular exercise the subject improved his cardiovascular health, which can be conventionally roughly, qualitatively, estimated by a comparison of peak heart rates. Indeed, the maximum heart rate at the peak exercise load from the first experiment to the second decreased by 16.4%, declining from 146 to 122. A conventional ST segment method also indicates the absence of ST depression, but did not provide any quantification of such an improvement since this ischemic range is sub-threshold for the method. Unlike such a conventional method, the method of the present invention did provide such quantification. Applying the current invention, the curves in FIG. 7 developed from the second experiment show that the area of a quasi-stationary, QT-RR interval hysteresis decreased significantly from the first experiment, and such hysteresis loop indicated that some level of exercise-induced ischemia still remained. A change in the shape of the observed composite dispersion-restitution curves also indicates an improvement since it changed from a flatter curve, similar to the flatter curves (with a lower excitability and a higher threshold, $v_r=0.3$ to $0.35$) in FIG. 2, to a healthier (less ischemic) more convex-shape curve, which is similar to the lower threshold curves ($v_r=0.2$ to $0.25$) in FIG. 2. Thus, FIG. 7 demonstrates that, due to its high sensitivity and high resolution, the method of the present invention can be used in the assessment of delicate alterations in levels of cardiac ischemia, indicating changes of cardiovascular health when treated by a conventional cardiovascular intervention.

EXAMPLE 7

Calculation of a Quantitative Indicium of Cardiovascular Health

Figure 8:
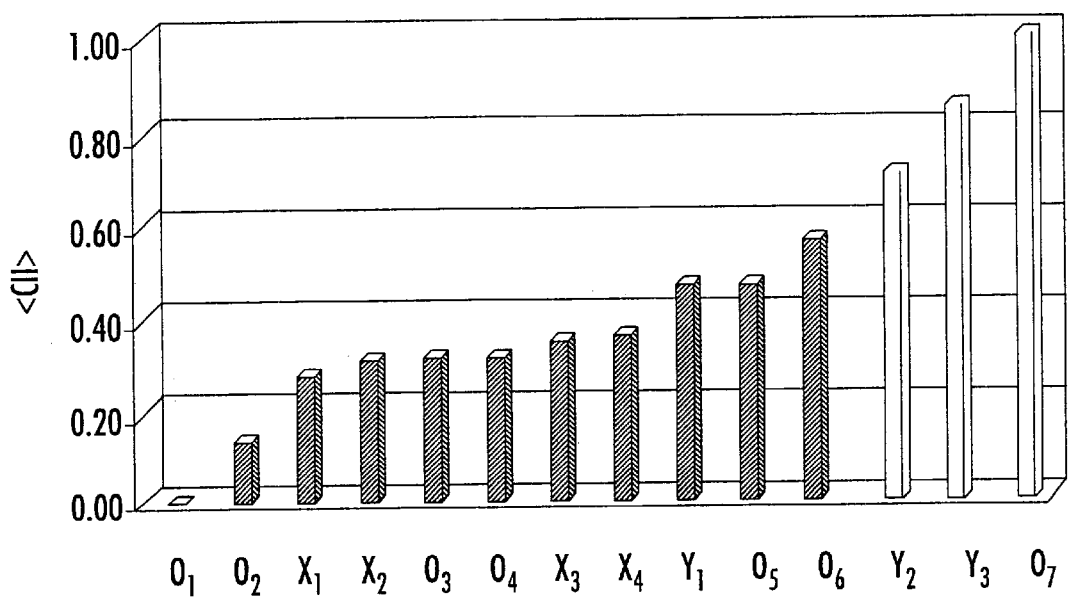
FIG. 8 illustrates a comparative cardiac ischemia analysis based on a particular example of a normalized measure of the hysteresis loop area. $<CII>=(CII-CII_{min})/(CII_{max}-CII_{min})$ ("CII" means "cardiac ischemia index"). $O_I$, $X_I$, and $Y_I$, represent human subject data. $X_i$ represents data collected from one subject (0.28–0.35) in a series of tests (day/night testing, run/walk, about two months between tests); exercise peak heart rate ranged from 120 to 135. $Y_i$ represents data collected from one subject (0.46–0.86) in a series of tests (run/walk, six weeks between tests before and after a period of regular exercise stage); exercise peak heart rate ranged from 122 to 146. Black bars indicate a zone ($<CII>$ less than 0.70) in which a conventional ST depression method does not detect cardiac ischemia. The conventional method may detect cardiac ischemia only in a significantly narrower range indicated by high white bars ($Y_2$, $Y_3$, $O_7$: $<CII>$ greater than 0.70).

This example was carried out with the data obtained in Examples 2–6 above. FIG. 8 illustrates a comparative cardiovascular health analysis based on ischemia assessment by the method of the present invention. In this example an indicium of cardiovascular health (here designated the cardiac ischemia index and abbreviated "CII") was designed, which was defined as a quasi-stationary QT-RR interval hysteresis loop area, S, normalized by dividing it by the product (T $T_{RR,min}$)($T_{QT,max}$-$T_{QT,min}$). For each particular subject this factor corrects the area for individual differences in the actual ranges of QT and RR intervals occurring during the tests under the quasi-stationary treadmill exercise protocol. We determined minimum and maximum CII in a sample of fourteen exercise tests and derived a normalized index <CII>=(CII−$CII_{min}$)/($CII_{max}$−$CII_{min}$) varying from 0 to 1. Alterations of <CII> in different subjects show that the method of the present invention allows one to resolve and quantitatively characterize different levels of cardiac and cardiovascular health in a region in which the conventional ST depression method is sub-threshold and is unable to detect any exercise-induced ischemia. Thus, unlike a rough conventional ST-segment depression ischemic evaluation, the method of the present invention offers much more accurate assessing and monitoring of small variations of cardiac ischemia and associated changes of cardiac or cardiovascular health.

EXAMPLE 8

Illustration of Rapid Sympatho-Adrenal Transients

Figure 9:
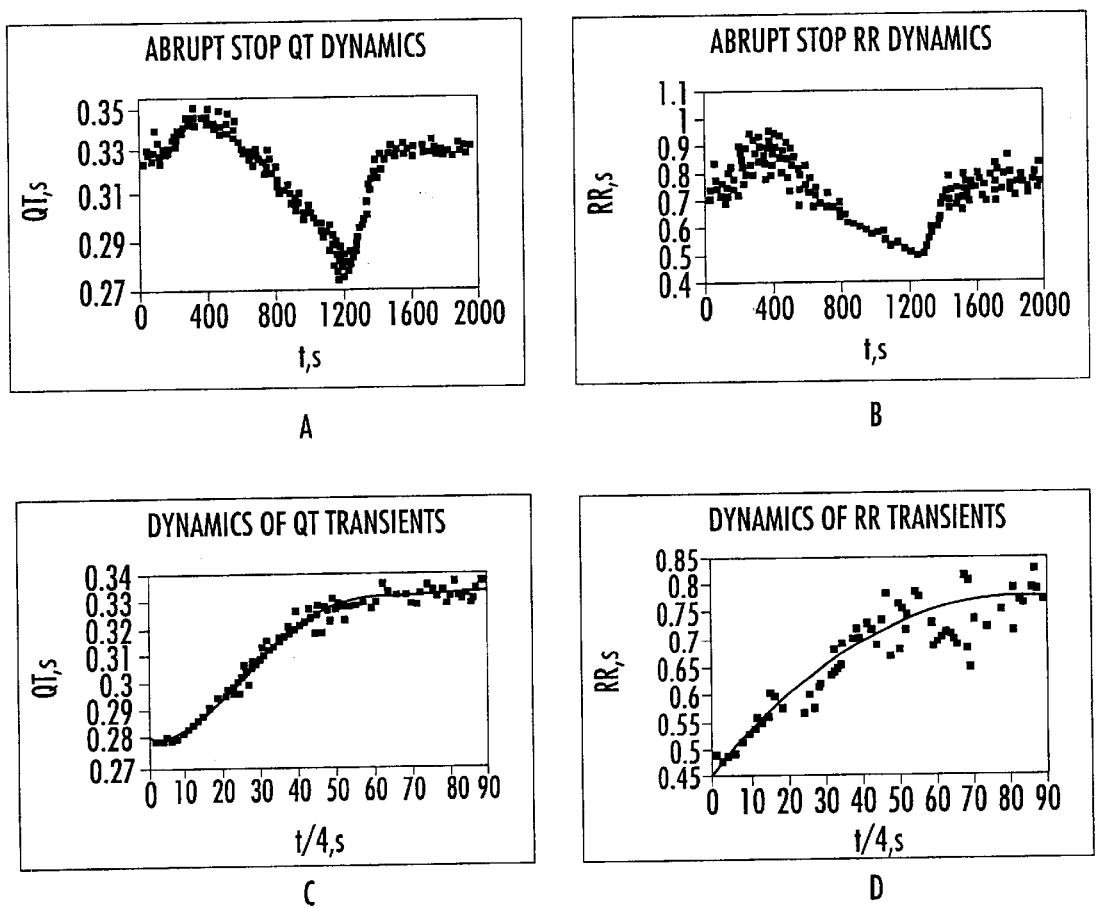
FIG. 9 illustrates a typical rapid peripheral nervous system and hormonal control adjustment of the QT and RR interval to an abrupt stop in exercise (that is, an abrupt initiation of a rest stage).

FIG. 9 illustrates a typical rapid sympathetic/parasympathetic nervous and hormonal adjustment of the QT (panels A, C) and RR (panels B, D) intervals to an abrupt stop after 10 minutes of exercise with increasing exercise load. All panels depict temporal variations of QT/RR intervals obtained from the right precordial lead V3 of the 12-lead multi-lead electrocardiogram. A sampling rate with which a waveform analyzer determined QT and RR intervals was equal to 15 samples per minute. A human subject (a 47 years-old male) was at rest the first 10 minutes and then began to exercise with gradually (during 10 minutes) increasing exercise load (Panels A, B-to the left from the RR, QT minima). Then at the peak of the exercise load (heart rate about 120 beat/min) the subject stepped off the treadmill in order to initialize the fastest RR and QT interval's adaptation to a complete abrupt stop of the exercise load. He rested long enough (13 minutes) in order to insure that QT and RR intervals reached post-exercise average stationary values. Panels C and D demonstrate that the fastest rate of change of QT and RR intervals occurred immediately after the abrupt stop of the exercise load. These rates are about 0.015 s/min for QT intervals while they vary from 0.28 s to 0.295 s and about 0.15 s/min for RR intervals while they grow from 0.45 s to 0.6 s. Based on the above-described experiment, a definition for "rapid sympatho-adrenal and hormonal transients" or "rapid autonomic nervous system and hormonal transients" may be given.

Rapid transients due to autonomic nervous system and hormonal control refer to the transients with the rate of 0.15 s/min for RR intervals, which corresponds to the heart rate's rate of change of about 25 beat/min, and 0.02 s/min for QT intervals or faster rates of change in RR/QT intervals in response to a significant abrupt change (stop or increase) in exercise load (or other cardiac stimulus). The significant abrupt changes in exercise load are defined here as the load variations which cause rapid variations in RR/QT intervals, comparable in size with the entire range from the exercise peak to the stationary average rest values.

EXAMPLE 9

Illustration of a Quasi-Stationary Exercise Protocol

Figure 10:
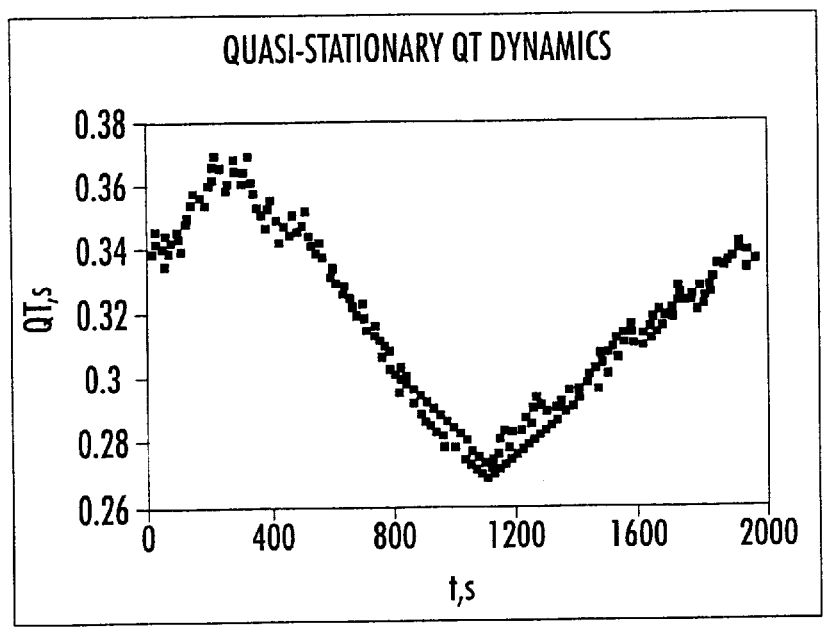
FIG. 10 illustrates a typical slow (quasi-stationary) QT and RR interval adjustment measured during gradually increasing and gradually decreasing cardiac stimulation.
Figure 10:
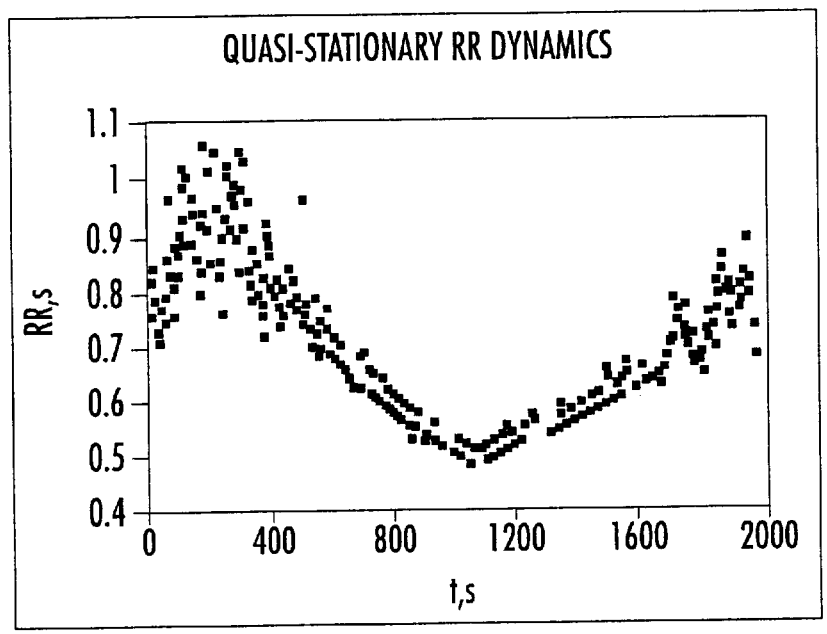
Figure 11:
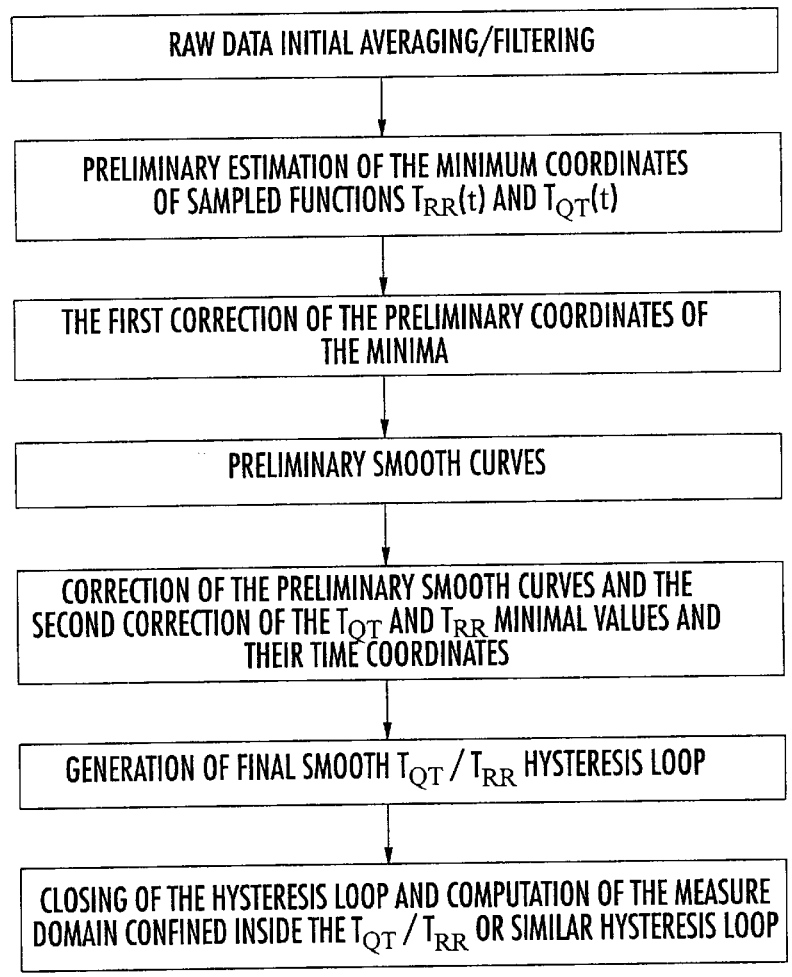
FIG. 11 demonstrates a block-diagram of the data processing by the method of optimized consolidation of a moving average, exponential and polynomial fitting (Example 10, steps 1–8).
Figure 13:
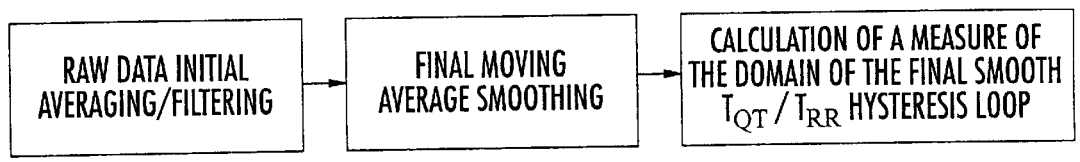
FIG. 13 demonstrates a block-diagram of the data processing by the method of a sequential moving average (Example 11, steps 1–3).

FIG. 10 illustrates a typical slow (quasi-stationary) QT (panel A) and RR (panel B) interval adjustment measured during gradually increasing and gradually decreasing exercise load in a right pre-cordial V3 lead of the 12 lead electrocardiogram recording. The sampling was 15 QT and RR intervals per minute. A male subject exercised during two consecutive 10 minute long stages of gradually increasing and gradually decreasing exercise load. Both QT and RR intervals gradually approached the minimal values at about a peak exercise load (peak heart rate ~120 beat/min) and then gradually returned to levels that were slightly lower than their initial pre-exercise rest values. The evolution of QT and RR intervals was well approximated by exponential fitting curves shown in gray in panels A and B. The ranges for the QT-RR interval, there-and-back, time variations were 0.34 s–0.27 s -0.33 s (an average rate of change ~0.005 s/min) and 0.79 s -0.47 s -0.67 s (an average rate of change ~0.032 s/min or ~6 beat/min) for QT and RR intervals, respectively. The standard root-mean-square deviation, a, of the observed QT and RR intervals, shown by black dots in both panels, from their exponential fits were on an order of magnitude smaller than the average difference between the corresponding peak and rest values during the entire test. These deviations were $\sigma$~0.003 s for QT and $\sigma$~0.03 s for RR intervals, respectively. According to FIG. 9 (panels C, D) such small perturbations, when associated with abrupt heart rate changes due to physiological fluctuations or due to discontinuity in an exercise load, may develop and decay faster than in 10 s, the time that is 60 times shorter than the duration of one gradual (ascending or descending) stage of the exercise protocol. Such a significant difference between the amplitudes and time constants of the QT/RR interval gradual changes and abrupt heart rate fluctuations allows one to average these fluctuations over time and fit the QT/RR protocol duration dynamics by an appropriate smooth exponential-like function with a high order of accuracy. A simultaneous fitting procedure (panels A, B) determines an algorithm of a parametrical time dependence elimination from both measured QT/RR data sets and allows one to consider QT interval for each exercise stage as a monotonic function.

Based on the above-described experiment a definition for a gradual, or "quasi-stationary" exercise (or stimulation) protocol, can be quantitatively specified: A quasi-stationary exercise (or stimulation) protocol refers to two contiguous stages (each stage 3, 5, 8 or 10 minutes or longer in duration) of gradually increasing and gradually decreasing exercise loads or stimulation, such as:

1. Each stage's duration is approximately an order of magnitude (e.g., at least about ten times) longer than the average duration (~1 minute) of a heart rate adjustment during an abrupt stop of the exercise between average peak load rate (~120–150 beat/min) and average rest (~50–70 beat/min) heart rate values.

2. The standard root-mean-square deviations of the original QT/RR interval data set from their smooth and monotonic (for each stage) fits are of an order of magnitude (e.g., at least about ten times) smaller than the average differences between peak and rest QT/RR interval values measured during the entire exercise under the quasi-stationary protocol.

As shown above (FIG. 10) a gradual quasi-stationary protocol itself allows one to substantially eliminate abrupt time dependent fluctuations from measured QT/RR interval data sets because these fluctuations have short durations and small amplitudes. Their effect can be even further reduced by fitting each RR/QT interval data set corresponding to each stage with a monotonic function of time. As a result the fitted QT interval values during each exercise stage can be presented as a substantially monotonic and smooth function of the quasi-stationary varying RR interval value. Presented on the (RR-interval, QT-interval)-plane this function gives rise to a loop, whose shape, area and other measures depend only weakly on the details of the quasi-stationary protocol, and is quite similar to the hysteresis loop presented in FIG. 2. Similar to a generic hysteresis loop, this loop can be considered as primarily representing electrical conduction properties of cardiac muscle.

It is well known that exercise-induced ischemia alters conditions for cardiac electrical conduction. If a particular individual has an exercise-induced ischemic event, then one can expect that the two experimental composite dispersion-restitution curves corresponding to the ascending and descending stages of the quasi-stationary protocol will be different and will form a specific quasi-stationary hysteresis loop. Since according to a quasi-stationary protocol the evolution of the average values of QT and RR intervals occurs quite slowly as compared with the rate of the transients due to sympathetic/parasympathetic and hormonal control, the hysteresis loop practically does not depend on the peculiarities of the transients. In that case such a hysteresis can provide an excellent measure of gradual ischemic exercise dependent changes in cardiac electrical conduction and can reflect cardiac health itself and cardiovascular system health in general.

It should be particularly emphasized that neither J. Sarma et al, supra, nor A. Krahn's et al. supra, report work based on collecting quasi-stationary dependences, which are similar to the QT-interval-RR interval dependence, since in fact both studies were designed for different purposes. To the contrary, they were intentionally based on non-quasi-stationary exercise protocols that contained an abrupt exercise stop at or near the peak of the exercise load. These protocols generated a different type of QT/RR interval hysteresis loop with a substantial presence of non-stationary sympatho-adrenal transients (see FIG. 9 above). Thus these prior art examples did not and could not include data which would characterize gradual changes in the dispersion and restitution properties of cardiac electrical conduction, and therefore included no substantial indication that could be attributed to exercise-induced ischemia.

EXAMPLES 10–12

Data Processing at Steps 44–45a, b (FIGS. 4A and 4B)

The following Examples describe various specific embodiments for carrying out the processing, shown in FIG. 4B, where the software implemented at steps 44b and 45b performs the following major steps:

(i) Generates sufficiently smooth time dependent QT and RR data sets by averaging/filtering and fitting these averaged data by exponential or any other suitable functions;

(ii) Combines into pairs the points of RR and QT data sets that correspond to the same time instants, thereby generating smooth QT/RR curves for the ascending and descending heart rate stages (branches) on the ($T_{RR}$, $T_{QT}$)-plane or a similar plane or its image in computer memory;

(iii) Closes the ends of the QT/RR curves to transform them into a closed loop and determines an area, S, or a similar measure of the domain confined by the said loop and computes an index to provide a quantitative characteristic of cardiovascular health in a human subject based on a measure of this domain.

Each of these three major steps may consist of several sub steps, as illustrated in each of the methods shown in FIG. 11, FIG. 13 and FIG. 15, FIG. 16 and as discussed in greater detail below.

EXAMPLE 10

A Method of Optimized Consolidation of a Moving Average, Exponential and Polynomial Fitting 1. Raw data Averaging/Filtering (Box 1 in FIG. 11).

The raw data set consists of two subsets $\{t_{RR}^i, T_{RR}^i\}$ i=1, 2, ... $N_{RR}$−1, and $\{t_{QT}^i, T_{QT}^i\}$, i=1, 2, ... $N_{QT}$−1, where $t_x^i$ and $T_x^i$ denote the i-th sampling time instant and the respective, RR or QT, interval duration (subscript x stands for RR or QT). In order to simplify the notation we shall omit the subscripts RR and QT when it is applicable to both sub-samples. It is convenient to represent each data point as a two-component vector $u_i=(t^i,T^i)$. The filtering procedure in this example comprises a moving averaging of neighboring data points. We shall denote a moving overage over a set of adjacent points by angular brackets with a subscript indicating the number of points included in the averaging operator. Thus, the preliminary data filtering at this sub step is described by the equation $$\langle u_i \rangle_2 = \frac{1}{2}\sum_{j=i}^{j=i+1} u_j = \frac{u_i + u_{i+1}}{2}, \qquad (10.1)$$

for each i=1, 2, ... N−1, where N is a number of data points in the corresponding (RR or QT) raw data set. Thus, the RR and QT interval durations and the corresponding sampling time points are identically averaged in order to preserve the one-to-one correspondence between them. This procedure removes the high frequency noise present in the raw data. This preliminary smoothing can also be described in the frequency domain and alternatively achieved via appropriate low-pass filtering. All the following processing pertinent to this example will be done on the averaged data points $<u_i>_2$ and the angular brackets will be omitted to simplify the notation.

2. Preliminary Estimation of the t-Coordinates of the Minima (Box 2 in FIG. 11).

The sub step consists of preliminary estimation of the time instants, $t^{im}_{RR}$ and $t_{QT}^{Jm}$ of the minima of the initially averaged RR-interval and QT-interval-data sets, respectively. The algorithm does a sequential sorting of the data sets choosing M data points corresponding to M least values of the RR- or QT-intervals and then averages the result. (In our examples, M=10.) First, the algorithm finds the u-vector $u_{i_1}=(t^{i_1},T^{i_1})$ corresponding to the shortest interval $T^{i_1}$. Next, this data point is removed from the data set $\{u_i\}$ and the algorithm sorts the remaining data set and again finds a u-vector $u_{i_2}=(t^{i_2},T^{i_2})$ corresponding to the shortest interval $T^{i_2}$. The minimum point is again removed from the data sets and sorting is repeated over and over again, until the $M^{th}$ u-vector $u_{i_m}=(t^m,T^{im})$ corresponding to the shortest interval $T^{im}$ is found. Next, the algorithm averages all M pairs and calculates the average minimum time coordinate $\bar{t}$ defined as $$\bar{t} = \frac{1}{M}\sum_{k=1}^{M} t^{ik} \qquad (10.2)$$

Finally, the algorithm determines the sampling time instant $t^{im}$, which is nearest to $\bar{t}$. We thus arrive to $t_{RRi}^m$ and $t_{QT}^{Jm}$ for RR and QT data sets, respectively.

3. The First Correction of the Coordinates of the Preliminary Minima (Box 3 in FIG. 11).

At this sub step the first correction to the minimum coordinates $t_{RR}^{im}$ and $t_{QT}^{Jm}$ is found. This part of the algorithm is based on the iterative exponential fitting of the T-component of the initially filtered data set $\{u_i\}=\{t^i, T^i\}$ by functions of the form $$T(t)=A \exp[\beta|t-t^m|], \qquad (10.3)$$

where $t^m$ is the time instant of the corresponding minimum determined at the previous sub step (i.e., to $t^m$−$t_{RR}^{im}$ for RR-intervals and $t^m=t_{QT}^{Jm}$ for QT-intervals). The fitting is done separately for the descending (t<$t^m$) and ascending (t>$t^m$) branches of u(t) with the same value of constants A and $t^m$ and different values of β for both branches. The initial value of A is taken from the preliminary estimation at sub step 2: A=$T^{im}$ and $t^m=t^{im}$ (i.e., A=$T_{RR}^{im}$, $t^m=t_{RR}^{im}$ for RR-intervals and A=$T_{QT}^{Jm}$, $t^m=t_{QT}^{Jm}$ for QT-intervals). The initial value of constant β for each branch and each data sub set is obtained from the requirement that the initial mean root square deviation σ=$σ_0$ of the entire corresponding branch from its fit by equation (10.3) is minimum in each subsequent iteration cycle new values of constants A and β are determined for each branch. At the beginning of each iteration cycle a constant A is taken from the previous step and the value of β is numerically adjusted to minimize the deviation value, σ. Such iterations are repeated while the mean square deviation σ is becoming smaller and are stopped when σ reaches a minimum value, σ=$σ_{min}$. At the end of this sub step the algorithm outputs the corrected values A and β and the respective values of a $σ_{min}^{RR}$ and $σ_{min}^{QT}$.

4. The Preliminary Smooth Curves (Box 4 in FIG. 11).

The sub step consists of calculating a series of moving averages over p consecutive points for each data subset $\{u\}$ as follows $$u_i^p \equiv \langle u_i \rangle_p = \frac{1}{p}\sum_{j=i}^{i+p-1} u_j. \qquad (10.4)$$

We shall refer to the quantity p as the width of the averaging window. The calculation is performed for different values of p, and then the optimum value of the width of the averaging window p=m is determined by minimizing the mean square deviation of the set $\{u_i^P\}=\{t_i^P, T_i^P\}$ from its fit by Eq. (10.3) with the values of parameters A, $t^m$, and, β determined at sub step 3. Having performed this procedure for each component of the data set (RR and QT) we arrive to the preliminary smoothed data set $\{u_i^m\}=\{t_i^m, T_i^m\}$, where $$T_i^m = \frac{1}{m}\sum_{j=i}^{i+m-1} T^i, \quad t_i^m = \frac{1}{m}\sum_{j=i}^{i+m-1} t^i \qquad (10.5)$$

The number of points in such a data set is $N_m=N-m+1$, where N is the number of data points after the initial filtering at sub step 1.

5. Correction of the Preliminary Smooth Curves and the second Correction of the QT and PR Minimal Values and its Coordinates (Box 5 in FIG. 11).

At this sub step we redefine the moving averages (using a smaller averaging window) in the vicinity of the minimum of quantity T (RR or QT interval). This is useful to avoid distortions of the sought (fitting) curve $T=T(t)$ near its minimum. The algorithm first specifies all data points $\{t^i, T^i\}$ such that $T^i$ lie between $$\min_i \{T^i\}$$

and $$\min_i \{T^i\} + \sigma_{\min}.$$

These data points have the superscript values i from the following set $$I = \left\{ i : T^i \in \left[\min_i \{T^i\}, \min_i \{T^i\} + \sigma_{\min}\right]\right\}. \qquad (10.6)$$

Let us denote by $i_0 \in I$ and $i_q \in I$ the subscript values corresponding to the earliest and latest time instants among $\{t_i\}$ ($i \in J$). We thus set $i_0=\min\{I\}$ and $i_q=\max\{I\}$. Denoting the number of points in such a set by $q_{RR}$ for the RR data and by $q_{QT}$, for the QT data we determine the width, q, of the averaging window as the minimum of the two, $q=\min\{q_{QT}, q_{RR}\}$. Now we write the moving average for the data points in the vicinity of the minimum as $$u_i^q \equiv \langle u_i \rangle_q = \frac{1}{q}\sum_{j=i}^{i+q-1} u_j \qquad (10.7)$$

Such modified averaging is applied to all consecutive data points $u_i$ with the subscript i ranging from $i_0$ to $i_q$. The final (smoothed) data set consists of the first $i_0-1$ data points defined by Eq.(10.4) with $i=, 2, \ldots i_0-1$, q points defined by Eq.(10.7) with $i=i_0, i_0+1, \ldots, i_q$, and $N-i_q-m$ points defined again by Eq.(10.4) with $i=i_q+1, i_q+2, \ldots, N-m+1$. This the final set $\{\bar{u}_i\}$ can be presented as $$\{\bar{u}_i\}=\{u_i^p:i\in\{1,2\ldots,i_0-1\}\cup\{i_q+1,\ldots,N-m+1\}\}\cup\{u_i^q:i\in\{i_0, i_0+1,\ldots,i_q\}\} \qquad (10.8)$$

At the end of sub step 10.5 the algorithm determines the final minimum values of QT and RR interval and the corresponding time instants. The algorithm sorts the smoothed data sets (10.8) and determines $\bar{u}_{min}$ ($\bar{t}_{min},\bar{T}_{min}$) corresponding to the minimum value of $\bar{T}_i$. This can be written as $$\bar{u}_{\min} \equiv \left\{(\bar{t}_{i_m}, \bar{T}_{i_m}) : \bar{T}_{i_m} = \min_k \{\bar{T}_k\}\right\} = \bar{u}_{i_m}. \qquad (10.9)$$

6. Final Fitting and the Final Smooth QT and RR Curves (Box 6 in FIG. 11).

At this sub step the parameters of functions representing final smooth QT and RR curves are found. First, each data set $\{\bar{u}_i\}$ is split into two subsets $\{\bar{u}_-\}$ and $\{u_+^i\}$ corresponding to the descending ($\bar{t}_i > \bar{t}_{i_m}$) and ascending ($\bar{t}_i \geq \bar{t}_{i_m}$) branch, respectively. We also shift the time origin to the minimum point ($\bar{t}_{i_m}$) and change the axis direction of the descending branch. These redefined variables are thus given by:

$$\{u_-^i\}=\{(t_-^i,T_-^i)\equiv(\bar{t}_{i_m}-\bar{t}_i,\bar{T}_i):i\leq i_m\}\}, \qquad (10.10a)$$

$$\{u_+^i\}=\{(t_+^i, T_+^i)\equiv(\bar{t}_i-\bar{t}_{i_m},\bar{T}_i):i\geq i_m\}. \qquad (10.10b)$$

Notice that the minimum point is included in both branches. Next we perform a linear regression by fitting each branch with a 4-th order polynomial function in the following form $$T_\pm(t_\pm)=a_\pm t_\pm^4+b_\pm t_\pm^3+c_\pm y_\pm^2+d \qquad (10.11)$$

The linear term is not included into this expression since this function must have a minimum at $t_\pm=0$. The value of d is defined by $$d=\bar{T}_{min} \qquad (10.12)$$

For computational convenience the variables $u_\pm$ are transformed into $z_\pm=T_\pm-d$ and then the coefficients $a_\pm$, $b_\pm$, and $c_\pm$ are determined from the condition that expression for the error $$\varepsilon = \sum_i \left[z_\pm^i - a_\pm(t_\pm^i)^4 - b_\pm(t_\pm^i)^3 - c_\pm(y_\pm^i)^2\right]^2 \qquad (10.13)$$

where summation is performed over all points of the corresponding branch, is minimized. We thus obtain four similar sets of linear algebraic equations-two for each of the $u_\pm$ branches of the two RR and QT data sets. These equations have the form $$\begin{Vmatrix} \sum(t_\pm^i)^8 & \sum(t_\pm^i)^7 & \sum(t_\pm^i)^6 \\ \sum(t_\pm^i)^7 & \sum(t_\pm^i)^6 & \sum(t_\pm^i)^5 \\ \sum(t_\pm^i)^6 & \sum(t_\pm^i)^5 & \sum(t_\pm^i)^4 \end{Vmatrix} \begin{Vmatrix} a_\pm \\ b_\pm \\ c_\pm \end{Vmatrix} = \begin{Vmatrix} \sum(t_\pm^i)^4 z_\pm^i \\ \sum(t_\pm^i)^3 z_\pm^i \\ \sum(t_\pm^i)^2 z_\pm^i \end{Vmatrix} \qquad (10.14)$$

All summations are performed over all points of the branch. Now the QT and RR interval time dependences curves can be presented as the follows $$T_{RR}(t) = \begin{cases} T_{RR}^-(t-t_{\min}^{RR}), & t \leq t_{\min}^{RR} \\ T_{RR}^+(t-t_{\min}^{RR}), & t \geq t_{\min}^{RR} \end{cases} \qquad (10.15)$$

and $$T_{QT} = \begin{cases} T_{QT}^-(t-t_{\min}^{QT}), & t \leq t_{\min}^{QT} \\ T_{QT}^+(t-t_{\min}^{QT}), & t \geq t_{\min}^{QT} \end{cases} \qquad (10.16)$$

where $T_{RR}^\pm(t)$ and $T_{QT}^\pm(t)$ are the fourth order polynomials given by Eq.(10.11) and $t_{min}^{RR}$ and $t_{min}^{QT}$ are the time coordinates of the corresponding minima defined by Eq. (10.9). Thus, formulas (10.10)–(10.16) determine the final smooth QT and RR curves with minima defined by formula (10.9).

7. Final Smooth Hysteresis Loop (Box 7 in FIG. 11).

At this sub-step the software first generates a dense (N+1)-point time-grid $\tau_k=t_{start}+k(t_{end}-t_{start})/N$, where k=0, 1, 2, ..., N (N=1000 in this example) and $t_{start}$ and $t_{end}$ are the actual values of time at the beginning and end of the measurements, respectively. Then it computes the values of the four functions $T_{RR}^{\pm}(\tau-t_{min}^{RR})$ and $T_{QT}^{\pm}(\tau-t_{min}^{QT})$ on the grid, which parametrically represents the final smooth curves $(T_{RR}^{\pm}(\tau-t_{min}^{RR}), T_{QT}^{\pm}(\tau-t_{min}^{QT}))$ in computer memory for the ascending (+) and descending (−) branches, respectively. This procedure is a computational equivalent of the analytical elimination of time. Next, the software also plots these smooth curves on the $(T_{RR},T_{QT})$-plane or on another, similar plane, such as $(f_{RR},T_{QT})$, where $f1/T_{RR}$ is the instantaneous heart rate. Finally, the algorithm adds to the curves a set of points representing a closing line, which connects the end point of the lower (descending) branch with the initial point on the of the upper (ascending) branch and, thus, generates a closed QT/RR hysteresis loop.

8. A Measure of the Domain Bounded by the QT/RR Hysteresis Loop (Box 8 in FIG. 11).

At this sub step a measure of the domain inside the QT/RR hysteresis loop is computed by numerically evaluating the following integral (see definition above):

$$S = \iint_\Omega \rho(T_{RR}, T_{QT}) dT_{RR} dT_{QT} \qquad (10.17)$$

where $\Omega$ is the domain on the $(T_{RR},T_{QT})$-plane with the boundary formed by the closed hysteresis loop, and $\tau(T_{RR}, T_{QT})$ is a nonnegative (weight) function. In this example we can take $\tau(T_{RR},T_{QT})=1$ so that S coincides with the area of domain $\Omega$, or we set $\rho=1/(T_{RR})^2$ so S coincides with the dimensionless area of the domain inside the hysteresis loop on the $(f,T_{QT})$-plane, where $f=1/T_{RR}$ is the heart rate.

EXAMPLE 11

A Method of a Sequential Moving Average

1. Raw Sata Averaging/Filtering.

The sub step (similar to 10.1) consists of raw data averaging (filtering) according to formula (10.4). This is performed for a preliminary set of values of the averaging window width, p.

2. Final Moving Average Smoothing.

The sub step includes subsequent final smoothing of the preliminary smoothed data represented by the set $\{u_i^p\}$ found at the previous step: as follows.

$$\overline{u^p} \equiv \langle u_i^p \rangle_{m_f} = \frac{1}{m_f} \sum_{j=i}^{j=i+m_f-1} u_j^p. \qquad (11.1)$$

Figure 12:
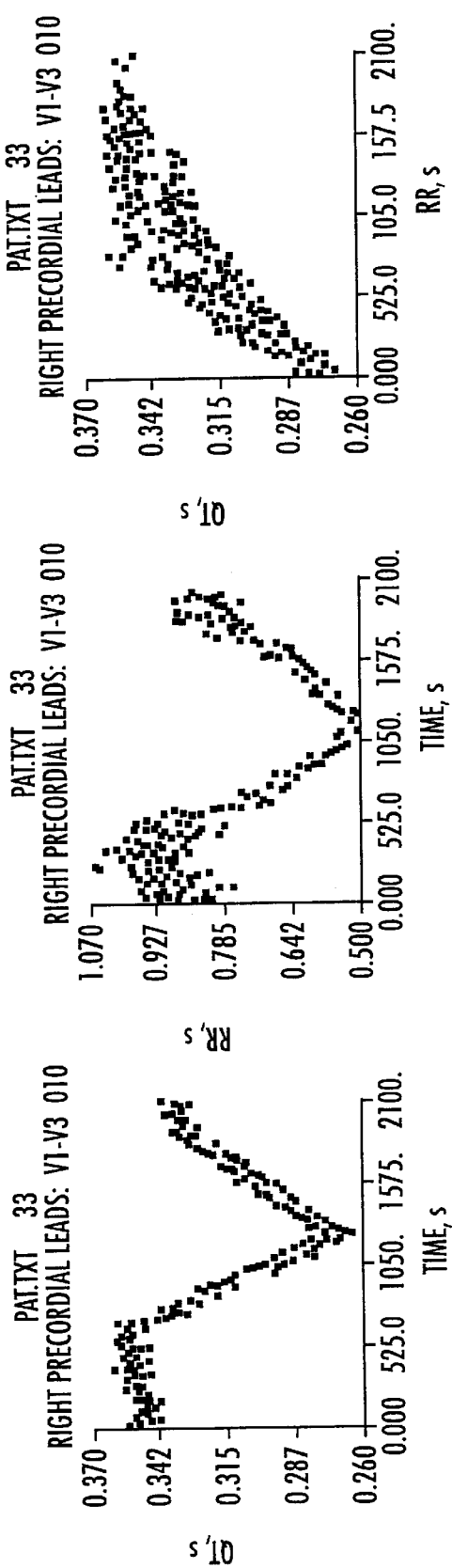
FIG. 12 demonstrates results of the processing throughout steps 1 to 8 of Example 10. Upper panels show QT and RR data sets processed from steps 1 to 3 (from left to right respectively), and the QT/RR hysteresis loop after step 1. The exponential fitting curves (step 3) are shown in gray in the first two panels. Low panels show the same smooth dependencies after processing from step 4 to a final step 8. Here the CII (see right low panel) is equal to a ratio $S/\{((T_{RR}^-(t_{end}-t_{min}^{RR})-T_{RR}^-(0))((T_{QT}^-(t_{start}-t_{minQT})-T_{QT}^+(0))\}$ (see example 10, section 7).
Figure 12:
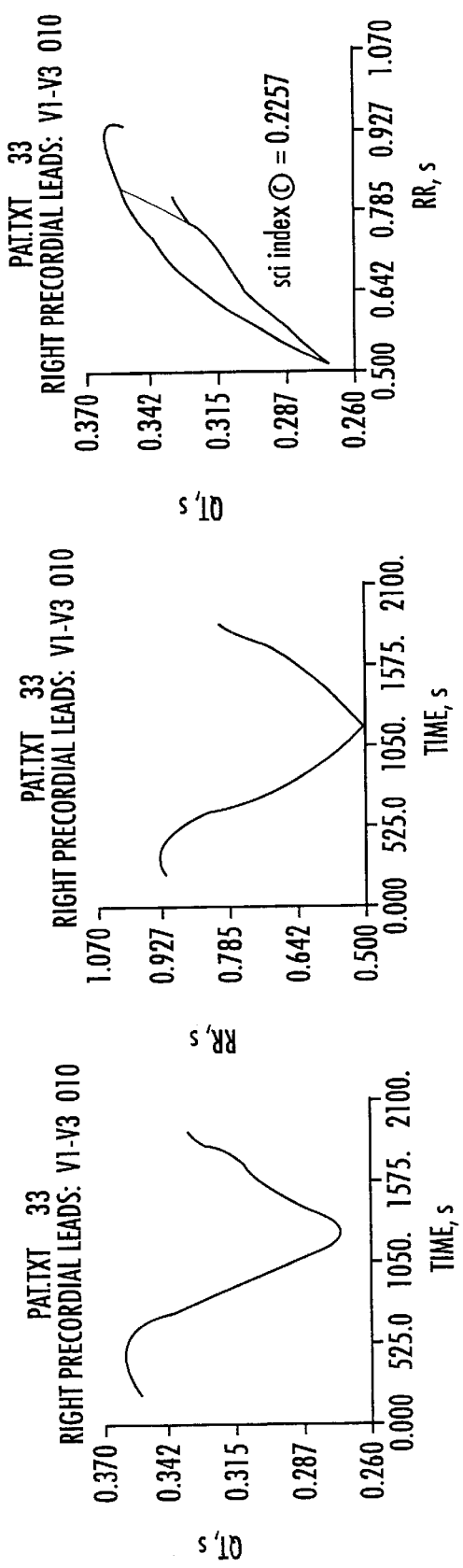
Figure 14:
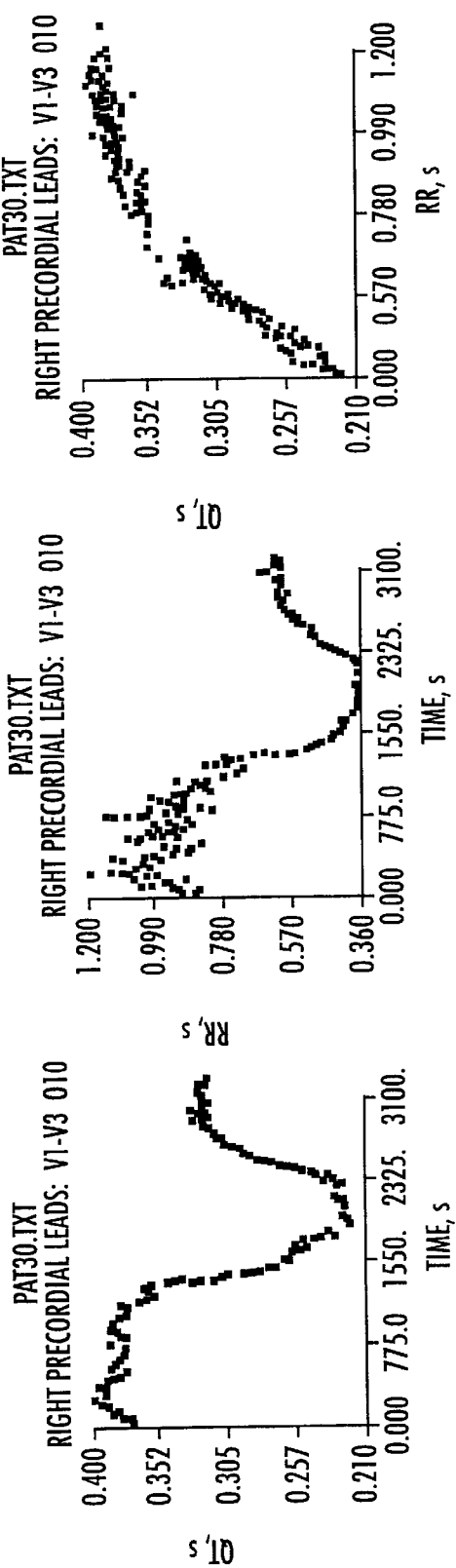
FIG. 14 demonstrates results of the processing throughout steps 1 to 2 of Example 11. Upper panels show processed QT and RR data sets, and the QT/RR hysteresis loop after step 1 (from left to right respectively). Low panels show the same smooth dependencies after the second moving average processing and a final step 3.
Figure 14:
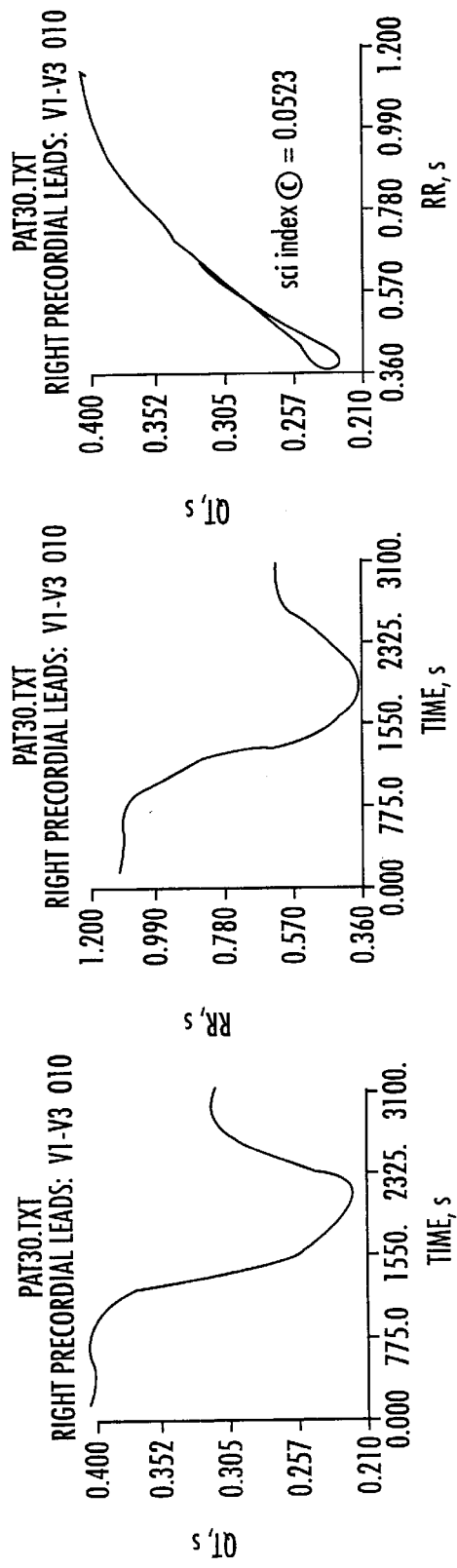

The window width $m_f$ is varied numerically to achieve optimum smoothness and accuracy of the fit. The optimally averaged data points form smooth curves on the corresponding planes (FIGS. 12, 14).

3. A Measure of the Domain Inside the QT/RR Hysteresis Loop.

The procedure on this sub step is as defined in Example 10, step 8, above.

EXAMPLE 12

A Method of Optimized Nonlinear Transformations

Figure 15:
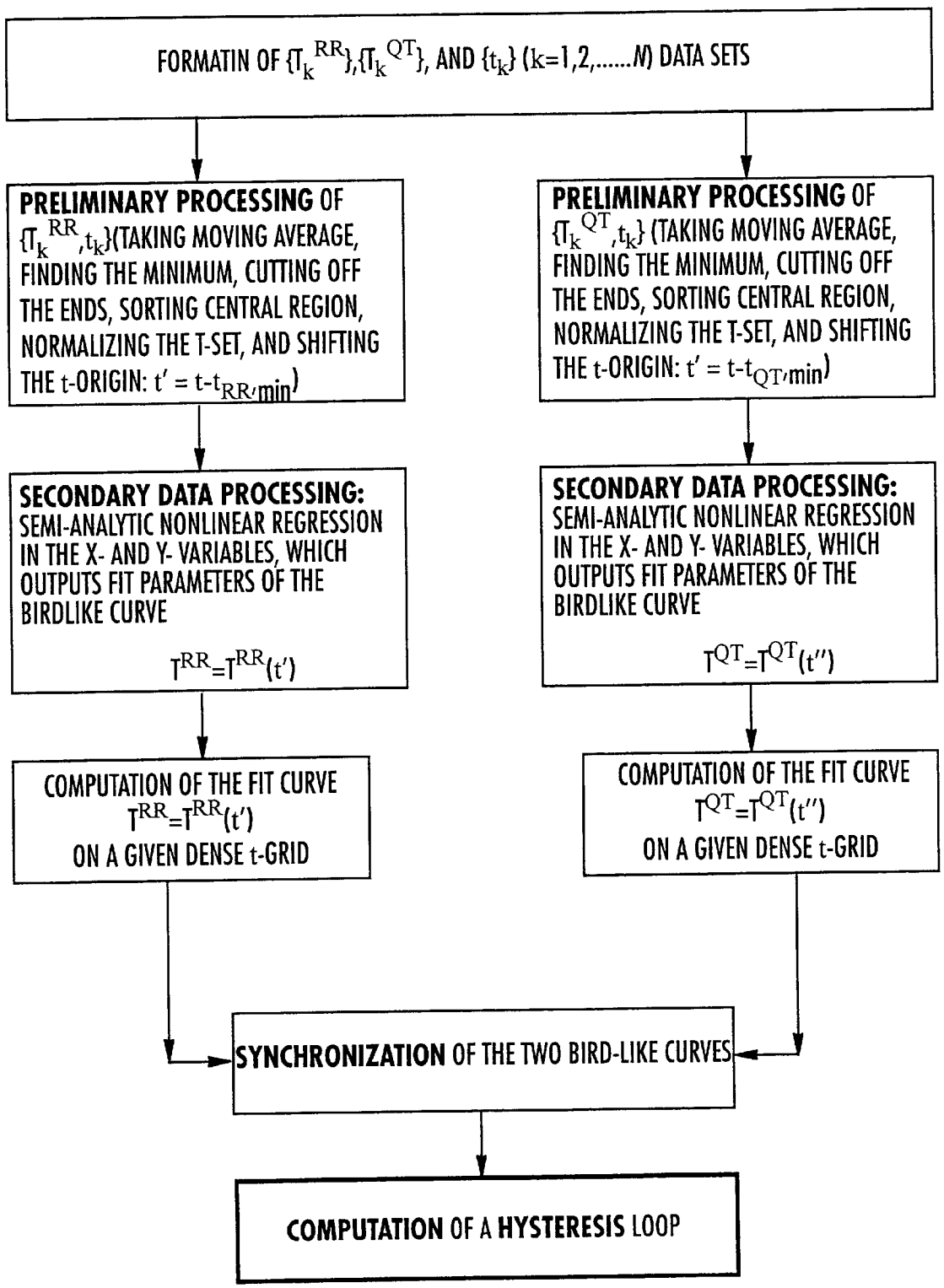
FIG. 15 shows a general data flow chart for major steps in optimized nonlinear transformation method. The left-hand side and the right-hand side boxes describe similar processing stages for the RR and QT-intervals, respectively.

FIG. 15 illustrates major steps in the data processing procedure involving our nonlinear transformations method. The first three stages for the RR and QT data sets are quite similar and each results in the computation of the fitted bird-like curves, $T^{RR}=T^{RR}(t)$ and $T^{QT}=T^{QT}(t)$, on a dense time-grid. Having computed both bird-like curves one actually completes the data processing procedure, because after appropriate synchronization, these two dependences parametrically along with a closing line represent the sought hysteresis loop on the $(T^{RR}, T^{QT})$, or similar, plane. We will describe our method in general terms equally applicable for the QT and RR interval data sets, and indicate the specific instants where there is a difference in the algorithm.

1. Preliminary Data Processing Stage.

Figure 16:
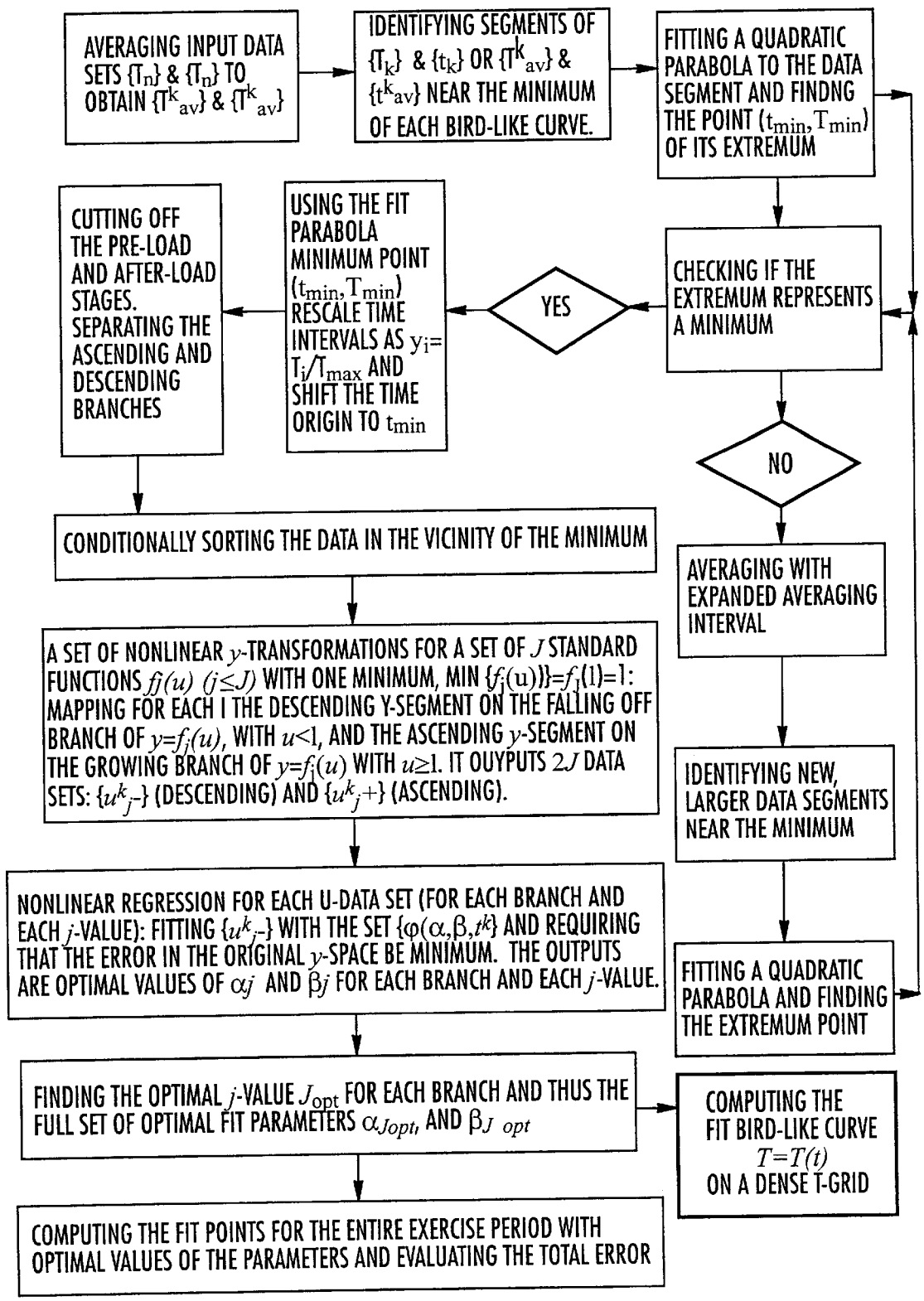
FIG. 16 shows a detailed data flow chart for one data subset, $\{t^k, T^K_{RR}\}$ $T_{RR}$I or $\{t^k, T^k_{QT}\}$ during stages (1 a/b) through (3 a/b) in FIG. 15. The preliminary stage, boxes 1 through 7, uses a combination of traditional data processing methods and includes: moving averaging (1), determination of a minimum region (2), fitting a quadratic parabola to the data in this region (3), checking consistency of the result (4), finding the minimum and centering data at the minimum (5) and (6), conditionally sorting the data (7). Stages (8) through (11) are based on the dual-nonlinear transformation method for the non-linear regression.

Let $\{T_k\}$, k=1, 2, N, be a set of the measured RR or QT interval durations, and $\{t_k\}$ be a set of the corresponding time instants, so that $t_i$ and $t_N$ are the starting and ending time instants (segments) of the entire record. The first three similar stages (stages 1 through 3 in FIG. 15) are the preliminary stage, the secondary, nonlinear-transformation stage, and the computational stage. A more detailed data flow chart for these stages is shown in FIG. 16. The preliminary stage, indicated by boxes 1 through 7 in FIG. 16, is a combination of traditional data processing methods and includes: smoothing (averaging) the data sets (1), determination of a region near the minimum (2), and fitting a quadratic parabola to the data in this region (3), checking consistency of the result (4), renormalizing and centering the data at the minimum (5), cutting off the data segments outside the exercise region and separating the ascending and descending branches (6), and finally filtering off a data segment in near the minimum (7). Let us discuss these steps in more detail.

Box 1 in FIG. 16, indicates the moving averaging and itself consists of two steps. First, we specify the initial value of the moving average procedure parameter m, as $$m = \max\left\{r\left(\frac{N}{N_c}\right), m_{\min}\right\} \qquad (12.1)$$

where r(x) is the integer closest to x, and the values of $N_c$ and $m_{min}$ are chosen depending on the number N of data points and the amount of random fluctuations in the data (the size of the random component in the data). In our examples we have chosen $N_c=100$ and $m_{min}=3$. The value of m can be redefined iteratively at the later stages and its choice will be discussed therein. Next we compute the moving average for $\{t_i\}$ and $\{T_i\}$ data sets with the given averaging parameter m as follows:

$$<t_k>_m = \frac{1}{m}\sum_{i=1}^{m} t_{k+i}, \quad <T_k>_m = \frac{1}{m}\sum_{i=1}^{m} T_{k+i} \qquad (12.2)$$

The subscript m will be omitted below if m is fixed and no ambiguity can arise. The next step in our algorithm is the initial determination of a time interval on which the parabolic fit will be performed, (the parabolic fit interval). This step is represented in FIG. 16 by Box 2. We note that this data subset can be redefined at a later stage if a certain condition is not satisfied. In the current realization of our algorithm this region defined differently for $\{t_i, T_i^{RR}\}$ and $\{t_i, T_i^{QT}\}$ data sets. For the data set $\{t_i, T_i^{RR}\}$ the initial parabolic fit segment is defined as the data segment $\{t_i, T^{RR}\}$ with all sequential values of i between $i^1$ and $i_2$ where $i_1=n_{min}-\Delta m$ and $i_2=n_{min}+\Delta m$, and the integer parameters $n_{min}$ and $\Delta m$ are defined as follows. The number $n_{min}$ determines the time instant $t_{n_{min}}$ among the original set of time instants which is the closest to the minimum on the averaged data set $\{<t_i>,<T_i>\}$. In other words, $t_{n_{min}}$ is the nearest to the average time instant $<t_M>$ which corresponds to the minimum value of the average RR-interval $<T_i^{RR}>$, that is, the time instant with the subscript value M defined by the condition $$<T_M^{RR}> = \min_i \{<T_i^{RR}>\} \qquad (12.3)$$

The value of $\Delta m$ is linked to the value of m by the condition $\Delta m=2$ m. The link between $\Delta n$ and m arises from the requirement that the algorithm is stable and consistent. The consistency is the requirement that the positions of the minimum of the curve obtained by moving averaging and by quadratic fitting were approximately the same. On the other hand, it is also important that the value of m is sufficiently small because quadratic fitting is done with the purpose to describe the data only locally in the immediate vicinity of the minimum.

For the data set $\{t_i, T_i^{QT}\}$ the initial parabolic fit segment is defined as the data subset that consists of all consecutive points belonging to the lower portion of the non-averaged $\{T_i^{QT}\}$ data set. We thus define $i_1$ as the first (minimum) number i such that $$T_i^{QT} \leq \min_j(T_j^{QT}) + R\left[\max_j(T_j^{QT}) - \min_j(T_j^{QT})\right] \qquad (12.4)$$

where R is a parameter, $0<R<1$, that determines the portion of the data to be fitted with the quadratic parabola. In our calculations we set $R=\frac{1}{8}=0.125$, so we fit with the parabola the data points that correspond to the bottom 12.5% of the interval durations. Thus, the subscript $i_1$ is the first (smallest) value of i such that condition (12.4) is satisfied. Similarly, $i_2$ is the last (greatest) value of i such that condition (12.4) is satisfied. The initial fit region is then defined as the following non-averaged data subset: $\{(t_i, T_i^{QT}): i=i_1, i_1+1, i_1+2, \ldots, i_2\}$. This method can also be used for determining an initial data segment for the quadratic polynomial fitting of the RR-data set.

At the next step, shown by box 3 in FIG. 12.2, we fit the data in this region (for each data set) by a parabola so that the data are approximately represented by the equation $$T_k = P_1 t_k^2 + P_2 t_k + P_3, \ k=j_1, j_1+1, j_1+2, \ldots, j_2. \qquad (12.5)$$

This is done using usual linear regression on this data subset. At the next step (Box 4 in FIG. 16) we check if the parabola has a minimum (i.e., if $P_1>0$). If this condition is satisfied, the determination of the parabolic fit interval and the fitting parabola itself is completed. Otherwise, we enter the loop indicated by boxes 1a through 3a in FIG. 16. The first step there is similar to the above second step utilized for the RR interval data set and defines an extended segment for the parabolic fitting. This is done by replacing m with m+1 and using this new value of m to redefine $\Delta m=2$ m and also calculate new averaged data sets in accordance with Eq. (12.2) as indicated by Box 1a in FIG. 16. This allows us to evaluate a new value of $n_{min}$ and new values of $i_1=n_{min}-\Delta m$ and $i_2=n_{min}+\Delta$ with new value of m (Box 2a). Then the parabolic fit is done again (Box 3a) and the condition $P_1>0$, that the parabola has a minimum, is checked again. If it is satisfied, the determination of the fit interval and the quadratic fit coefficients procedure is completed. Otherwise we replace m with m+1 and repeat the process again and again until the condition $P_1 \geq 0$ is satisfied. This condition ensures that the extremum of the quadratic parabola is a minimum indeed. By the very design of the exercise protocol the average heart rate reaches a certain maximum somewhere inside the load stage and therefore corresponding average RR-interval reaches a minimum. This ensures that a so-defined data segment exists and is unique, and therefore the coefficients of the quadratic parabola are well defined. In short, we use the shortest data segment that is centered around the minimum of the averaged data set and that generates a quadratic parabola with a minimum ($P_1>0$).

The parabolic fit defines two important parameters of the data processing procedure, the position ($t_{min}, T_{min}$) of the minimum on the (t,T)-plane as follows $$t_{min} = -\frac{P_2}{2P_1}, \quad T_{min} = P_3 - \frac{P_2^2}{4P_1}. \qquad (12.6)$$

These parameters are final in the sense that our final fit curve will always pass through and have a minimum at the point ($t_{min}, T_{min}$). The coordinates ($t_{min}, T_{min}$) thus constitute parameters of our final fit bird-like curve. Having found the ordinate $T_{min}$ of the minimum we can renormalization of the T-data set as follows:

$$y_k = \frac{T_k}{T_{min}}. \qquad (12.7)$$

We also take the abscissa of the parabola's minimum $t_{min}$ as the time origin and define the time components of the data points as follows $$t_i^- = t_i - t_{min}, t_i^- > 0, t_j^+ = t_j - t_{min}, t_j^+ > 0. \qquad (12.8)$$

These two data transformations are indicated by Box 5 in FIG. 16. We also restrict the data set only to the exercise period, plus some short preceding and following intervals (Box 5). The conditions $t_i^- \leq 0$, and $t_j^+ >$ define the descending, $\{t_i^-, T_i\}$, and ascending, $\{t_j^+, T_j\}$, branches, respectively, so the corresponding data points can be readily identified and separated (Box 6). Given the durations $t_d$ and $t_a$ of the descending and ascending load stage, respectively, we can reduce the original set by cutting off the points on the descending branch with $t_j^+ < -t_d$ and the points on the ascending branch with $t_j^{+>t_a}$ (Box 6 in FIG. 16). This determines the minimum value $i_0$ of subscript i for the descending branch, and the maximum value $j_{max}$ of subscript j on the ascending branch.

The final step of the preliminary data processing is the conditional sorting (Box 7). The conditional sorting removes all consecutive points such that at least one of them falls below the minimum of the parabola. The removal of the points below the minimum is necessary because the nonlinear transformation is possible only when $y_i \geq 1$. Eliminating only separate points below the minimum y=1 would create a bias in the data. Therefore, we have to eliminate an entire segment of the data in the vicinity of the minimum. It should be remembered though, that these points have already been taken into account in the above quadratic filtering procedure that determines ($t_{min}, T_{min}$) via Eq. (12.6).

Thus, the preliminary data processing results in two data sets corresponding to the descending and ascending load stages. The descending data set is defined as a set of consecutive pairs $(t_i^-, y_i) \equiv (t_i^-, y_i^-)$ with $i=i_0, i_0+1, i_0+2, \ldots, i_{max}$, where $i_{max}$ is determined by the conditional sorting as the largest subscript i value still satisfying the condition $y_i \geq 1$. Similarly, the ascending data set is defined as a set of consecutive pairs $(t_i^+, y_i^+) \equiv (t_i^+, y_i^+)$ with $j=j^{min}, j_0+1, j_0+2, \ldots, j_{max}$, where $j_{min}$ is determined by the conditional sorting as the first subscript j value on the ascending branch starting from which the condition $y_j>1$ is satisfied for all subsequent j.

2. Secondary Data Processing.

At the second stage we introduce a fundamentally new method of nonlinear regression by means of two consecutive optimal nonlinear transformations. The idea of the method is to introduce for each branch two appropriate nonlinear transformations of the dependent and independent variables, $y=j(u)$ and $u=\phi(t)$, both transformations depending on some parameters, and choose the values of the parameters in such a way that the composition of these transformations $f(\phi(t_i))$ would provide an approximation for $y_i$. Let $(t_i^-, y_i^-)$ and $(t_i^+, y_i^+)$ be the cut, conditionally sorted and normalized data set corresponding to the descending and ascending branches representing the dynamics of the RR- or QT-intervals during exercise. The nonlinear transformation $y \Rightarrow u$ is defined via a smooth function $$y = f_\gamma(u), \qquad (12.9)$$

that has a unit minimum at $u=1$, so that $f_\gamma(1)=1$, $f_\gamma'(1)=0$, and $f_\gamma(u)$ grows monotonously when $u \geq 1$ and decreases monotonously when $u \leq 0$. The subscript y represents a set of discrete or continuous parameters and indicates a particular choice of such a function. Let us denote by $f_\gamma^-(u)$ the monotonously decreasing branch of $f_\gamma(u)$ and its monotonously increasing branch, by $f_\gamma^+(u)$. We can thus write $$f_\gamma(u) = \begin{cases} f_\gamma^-(u), & \text{when } u \leq 1, \\ f_\gamma^+(u), & \text{when } u \geq 1. \end{cases} \qquad (12.10)$$

Let $u=g_\gamma^+(y)$ and $u=g_\gamma^-(y)$ be the inverse functions for the respective branches of $f_\gamma(u)$. The functions $g_\gamma^+(y)$ and $f_\gamma^+(u)$ are monotonously increasing, while the functions $g_\gamma^-(y)$ and $f_\gamma^-(u)$ are monotonously decreasing. Let $\{t_i, y_i^-\}$ represent the data for the descending segment of the data set, i.e. $t_i < t_{min}$ and $\{t_i, y_i^+\}$ represent the data for the ascending segment of the data set i.e. for $t_i > t_{min}$. The transformation $$u_{\gamma, i}^- = g_\gamma^-(y_i^-) \qquad (12.11)$$

maps the monotonously decreasing (on the average) data set $\{t_i, y_i^-\}$ into a monotonously increasing one:

$$\{t_i, y_i^-\} \Rightarrow \{t_i, g_\gamma^-(y_i^-)\} \equiv \{t_i, u_{\gamma, i}^-\}. \qquad (12.12)$$

Moreover, the average slope of the original data set is decreasing as $t_i$ approaches $t_{min}$ and eventually vanishing at the minimum. In contrast, the average slope of the transformed data set is always nonzero at $t=t_{min}$. Similarly, the transformation $$u_{\gamma, i}^- = g_\gamma^-(y_i^-) \qquad (12.13)$$

maps the monotonously increasing (on the average) data set $\{t_i, y_i^+\}$ into a monotonously increasing one:

$$\{t_j, y_j^-\} \Rightarrow \{t_j, g_\gamma^+(y_j^+)\} \equiv \{t_j, u_{\gamma, j}^+\}. \qquad (12.14)$$

In our examples we used a discrete parameter γ taking two values γ=1 and γ=2 that correspond to two particular choices of the nonlinear y-transformation. The first case (γ=1) is described by the equations $$y = f_1(u) \equiv 1+(u-1)^2; \; u^- = g_1^-(y) = y - \sqrt{y^2-1}, \; u^+ = g_1^+(y) = y + \sqrt{y^2-1} \quad (12.15)$$

The second case, γ=2, is described by the equations $$y = f_2(u) \equiv u + \frac{1}{u}; \qquad (12.16)$$

$$u^- = g_2^-(y) \equiv 1 - \sqrt{y-1},$$

$$u^+ = g_2^+(y) \equiv 1 + \sqrt{y-1}.$$

Both functions reach a minimum $y=1$ at $u=1$. An example of such a function depending on a continuous parameter $\gamma>0$ is given by $$f_\gamma(u) = A_\gamma \left\{ \frac{1}{\gamma^2 + b_\gamma u} + \frac{\gamma^2 b_\gamma u}{\gamma^2 b_\gamma u + 1} \right\}, \qquad (12.17)$$

$$b_\gamma \equiv 1 + \gamma + \frac{1}{\gamma}.$$

The parameter $b_\gamma$ has been determined from the condition that $f_\gamma(u)$ has a minimum at $u=1$ and the coefficient $A_\gamma$ is determined by the condition $f_\gamma(1)=1$, which yields $$A_\gamma = \frac{\gamma^3 + \gamma^2 + \gamma + 1}{\gamma^3 + \gamma^2 + 2\gamma} \qquad (12.18)$$

Figure 17:
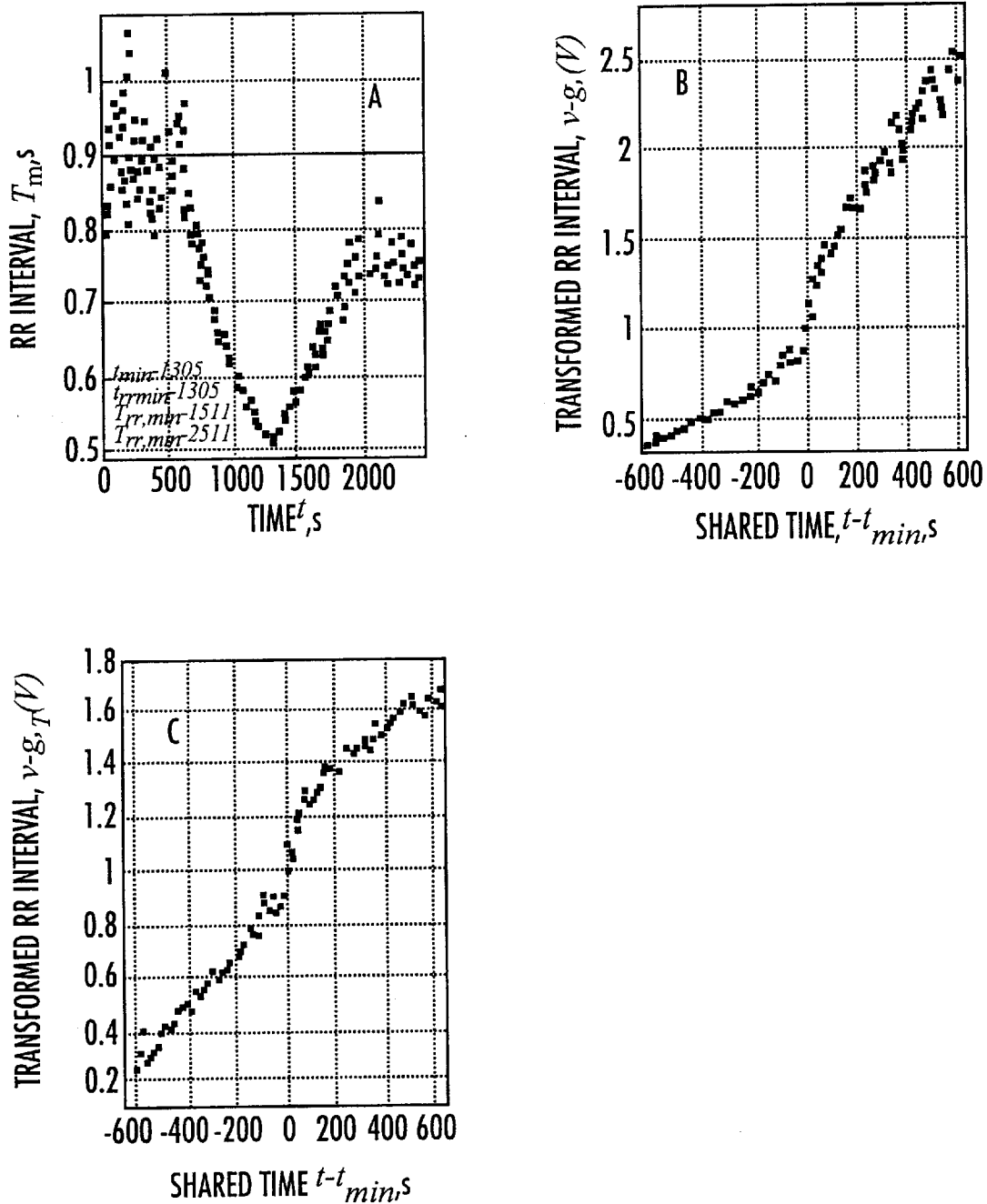
FIG. 17 displays the nonlinear transformation of a filtered RR-interval data set. Panel A shows the data on the original (t,y)-plane, the minimum is marked with an asterisk inside a circle. Panels B and C show the transformed sets on the (t,u)-plane, for j=1 and for j=2, respectively. The image of the minimum is also marked with an encircled asterisk. Note that the transformed data sets concentrate around a monotonously growing (average) curve with a clearly linear portion in the middle.
Figure 18:
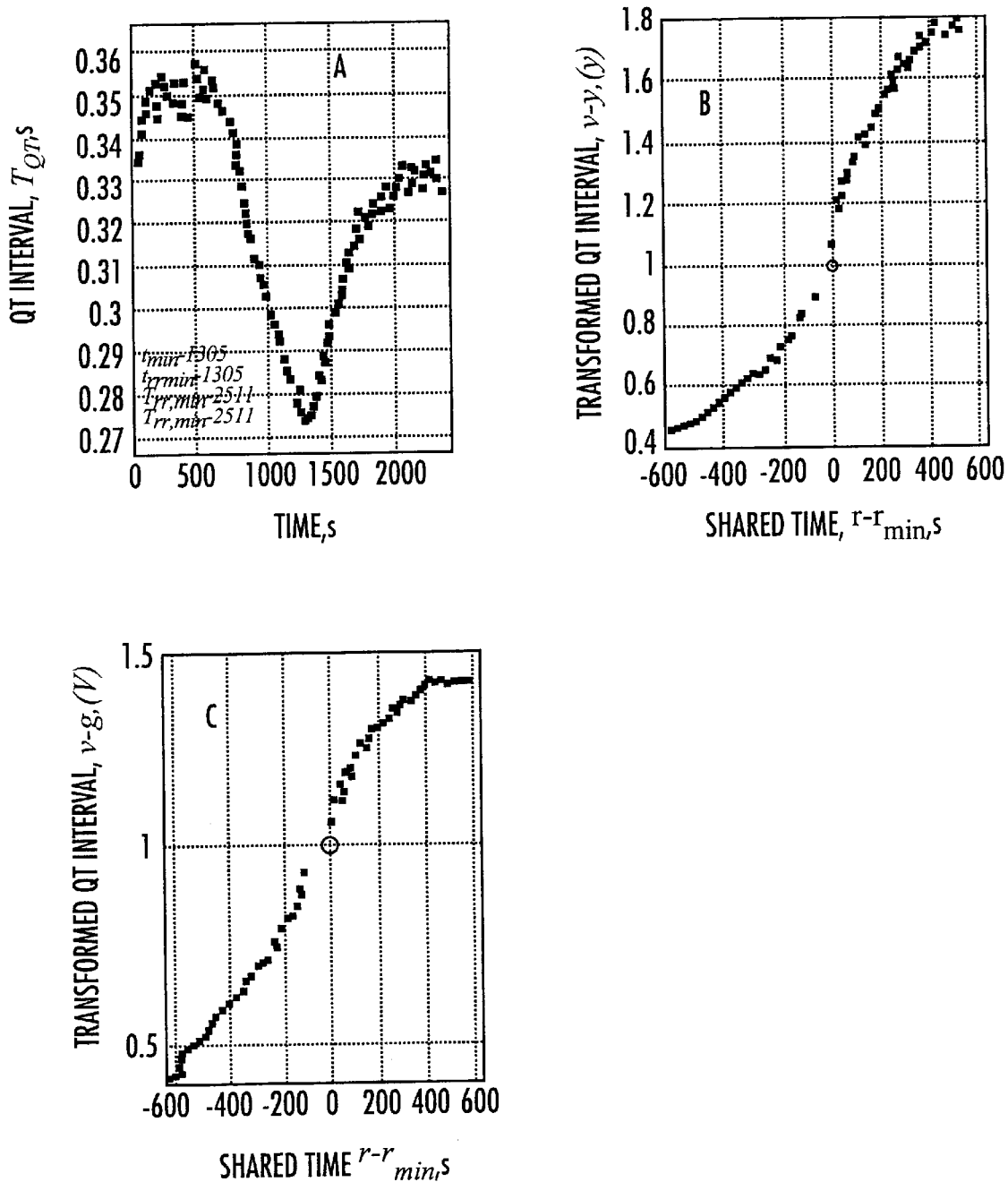
FIG. 18 is similar to FIG. 17 but for a QT-interval data set.

In our numerical examples below we utilize the discrete parameter case with γ taking two values, 1 and 2. The original and transformed sets are shown in FIGS. 17 (RR intervals) and 18 (QT-intervals). Panels A in both figures show the original data sets on the (t,T)-plane and panels B and C show the transformed sets on the (t,u)-plane, for γ1 and for γ=2, respectively. The parabola minima on panels A and C are marked with a circled asterisk. The original data points concentrate near a non-monotonous curve (the average curve). The data points on the transformed plane concentrate around a monotonously growing (average) curve. Moreover, the figure illustrates that the transformation changes the slope of the average curve in the vicinity of $t=t_{min}$ from zero to a finite, nonzero value. On the $(t-t_{min}, u)$-plane the point corresponding to the parabola's minimum is (0, 1). This point is also marked by a circled asterisk on panels B and C of FIGS. 17 and 18.

Let us introduce a pair of new time variables $\tau^-$ and $\tau^+$ for the descending and ascending branches, respectively. We shall count them off from the abscissa of the minimum of the fitted parabola and set $$\tau_i^- = t_{min} - t_i, \; t_i \leq t_{min}, \; i=1, 2, \ldots, I^-\tau_j^+ = t_j - t_{min}, \; t_j \geq t_{min}, \; j=1, 2, \ldots J^+ \qquad (12.19)$$

where $I^-$ and $J^+$ are the number of data points on the descending and ascending branches, respectively. The (formerly) descending branch can be treated in exactly the same way as the ascending one if simultaneously with the time inversion given by the first line in Eq. (12.19) we perform an additional transformation of the descending branch ordinates as follows $$v^k = 1 - u_k^-. \qquad (12.20)$$

In these variables both branches $(\tau_i^-, v_i)$ and $(\tau_j^+, u_j^+)$ are monotonously growing and start from the same point ($\tau=0$, u=1) at which both have nonzero slope and possess similar behavior (convexity).

Since both branches are treated in exactly the same way, we shall simplify the notation and temporarily omit the superscripts ± and write $(\tau_k, u_k)$ for any of the pairs $(\tau_i^-, v_i)$ or $(\tau_j^+, u_j^+)$. We shall fit the data set $\{u_k\}$ with $\{\phi(\alpha, \beta, \tau_k)\}$, that is represent $\{u_k\}$ as $$u_k \approx \phi(\alpha, \beta, K, \tau_k) \qquad (12.21)$$

where the function $\phi$ depends linearly on K and is defined as $$\phi(\alpha, \beta, K, \tau) = 1 + K\xi(\alpha, \beta, t) \qquad (12.22)$$

where $$\xi(\alpha, \beta, \tau) = \begin{cases} \dfrac{\alpha}{\beta}\left(1 + \dfrac{\tau}{\alpha}\right)^\beta & \text{when } \beta > 0 \\ s \equiv \alpha \ln\left(1 + \dfrac{\tau}{\alpha}\right) & \text{when } \beta = 0 \\ \dfrac{\alpha}{1+\beta}\left[\left(1 + \dfrac{s}{\alpha}\right)^{1+\beta} - 1\right] & \text{when } -1 \leq \beta < 0 \end{cases}$$

Figure 19:
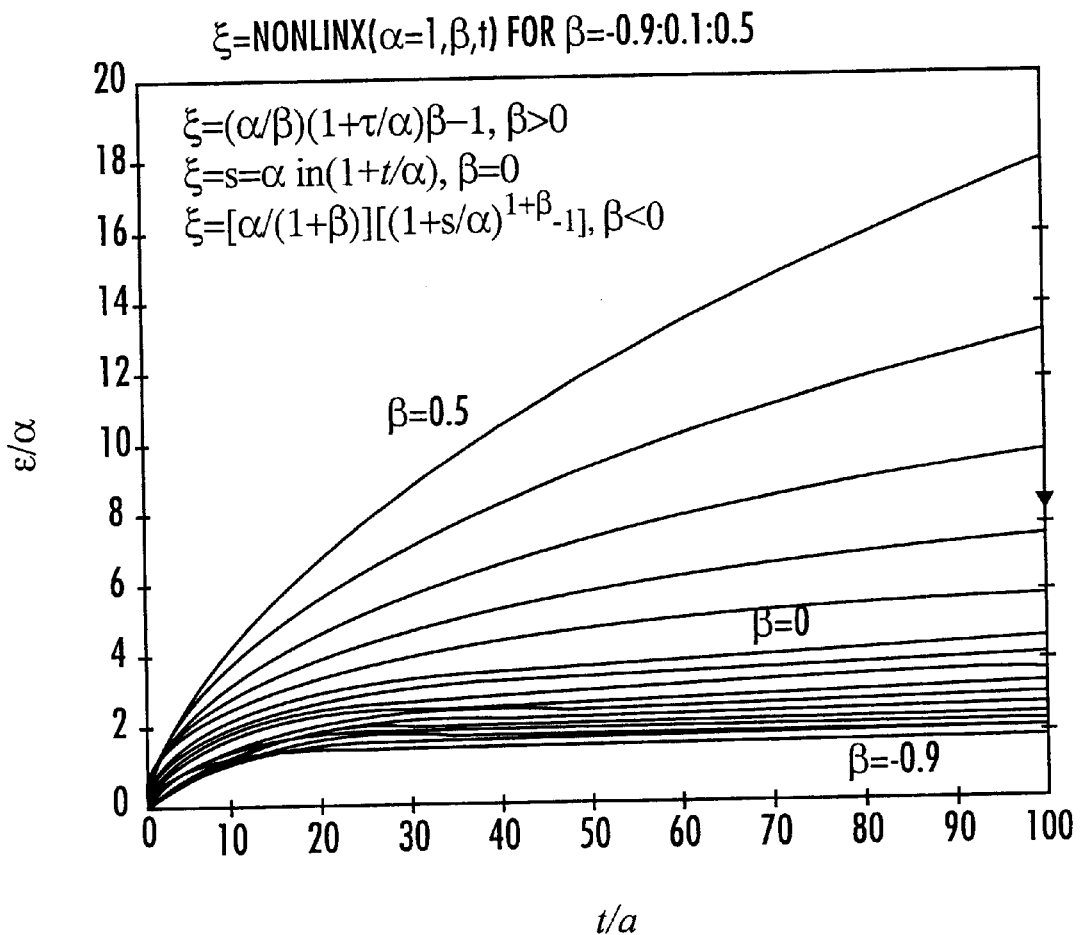
FIG. 19 displays an appropriately scaled representation for the family of functions $\xi(\alpha, \beta, \tau)$ for fifteen values of parameter $\beta$ varying with the step $\Delta\beta=0.1$ from $\beta=-0.9$ (lower curve) through $\beta=0$ (medium, bold curve), to $\beta=0.5$ (upper curve). The function $\xi(\alpha, \beta, \tau)$ is continuous in all three variables and as a function of $\tau$ has a unit slope at $\tau=0$, $\xi'(\alpha, \beta, 0)=1$.

A family of functions $\xi(\alpha, \beta, \tau)$ is shown in FIG. 19 for fifteen values of parameter $\beta$. The parameter $\alpha$: is completely scaled out by plotting the function on the plane $(\tau/\alpha, \epsilon/\alpha)$. The function $\xi(\alpha, \beta, \tau)$ is continuous in all three variables and as a function of $\tau$ at fixed $\alpha$ and $\beta$ has a unit slope at $\tau=0$, $\xi'(\alpha, \beta, 0)=1$. Therefore, at $\tau \to 0$ the function $\xi$ possesses a very simple behavior, $\xi \sim \tau$, which is independent of $\alpha$ and $\beta$ (the size of the region of such behavior of course depends on $\alpha$ and $\beta$). The function $\xi$ possesses the following important feature: when $\beta$ passes through the point $\beta=0$, its asymptotic behavior at $\tau \to \infty$ continuously changes from the power function $\xi \sim \tau^\beta$ at $\beta>0$, through $\xi \sim \ln(\tau)$ at $\beta=0$, to a power of the logarithm, $\xi \sim \ln^{1+\beta}(\tau)$ when $-1<\beta<0$. When $\beta \to -1$, the behavior of $\xi$ changes once more, and becomes $\xi \sim \ln(\ln(\tau))$. The convexity of any function of the family is the same when $\beta<1$.

We shall explicitly express parameter K via $\alpha$ and $\beta$ using the requirement for a given pair of $\alpha$ and $\beta$ Eq-s. (12.22) and (12.23) ensure the best data fit in the u-space in a certain vicinity of the point $(\tau=0,u=1)$. Let $K_1$ be the number of points where the fit is required. The corresponding quadratic error is then a function of K, $\alpha$ and $\beta$ that can be written as $$\varepsilon^{(u)}(K, \alpha, \beta) = \sum_{k \leq K_1} [u_k - K\varphi(\alpha, \beta, T_k)]^2 \qquad (12.24)$$

and the requirement of its minimum immediately yields the following expression for K $$K = K(\alpha, \beta) \equiv \frac{\sum_{k \leq K_1} u_k \varphi(\alpha, \beta, \tau_k)}{\sum_{k \leq K_1} \varphi^2(\alpha, \beta, \tau_k)} \qquad (12.25)$$

In our calculations we used such $K_1$ value that would include all adjacent points with the values of u between u=1 and u=1+0.4 $(u_{max}-1)$. We have thus reduced the number of fitting parameters in our fitting procedure to two continuous parameters, $\alpha$ and $\beta$, and one discrete parameter, $\gamma$. The fitting function thus becomes $$y_k \approx f_\gamma(1 + K(\alpha,\beta)\xi(\alpha,\beta,\tau_k)) \qquad (12.26)$$

The values of parameters $\alpha$, $\beta$ and K (and $\gamma$) are now directly determined by the condition that the fit error in the y-space $$\varepsilon_\gamma^{(y)}(\alpha, \beta) = \sum_K [y_k - f_\gamma(1 + K(\alpha, \beta)\varphi(\alpha, \beta, \tau_k))]^2 \qquad (12.27)$$

is minimum. The sum in Eq. (12.27) is evaluated numerically on a grid $(\alpha, \beta)$ values for $\gamma$ equal 1 and 2. Then the values of $\alpha$, $\beta$ and $\beta$ that deliver a minimum to $\epsilon_\gamma^{(y)}$ are found via numerical trials. Calculations can then be repeated on a finer grid in the vicinity of the found minimum.

Having found parameters $\alpha^{min}$, $\beta_{min}$ and $\gamma_{min}$ for the ascending branch we generate a dense t-grid $\{t_s, s=1, 2, \ldots, N\}$ and calculate the corresponding values of the interval duration as $$T_s = T_{min} f_{\gamma_{min}}(1 + K(\alpha_{min}, \beta_{min})\xi(\alpha_{min}, \beta_{min}, t_s - t_{min})). \qquad (12.26)$$

Figure 20:
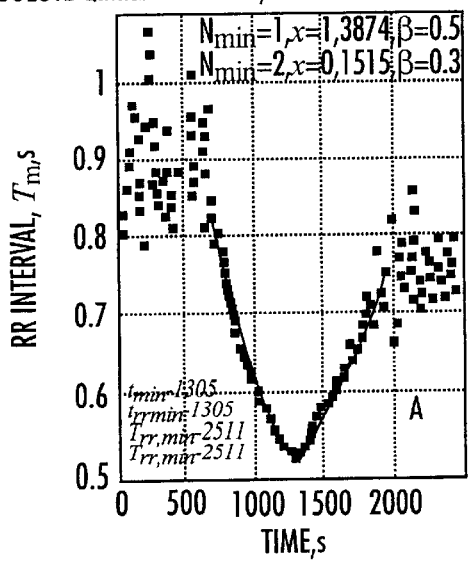
FIG. 20 shows an example of full processing of the RR and QT data sets for one patient. Panels A and C represent RR and QT data sets and their fit. Panel B shows the corresponding ascending and descending curves and closing line on the $(T_{RR}, T_{QT})$-plane, on which the area of such a hysteresis loop has the dimension of time-squared. Panel D shows a hysteresis loop on the $(f_{RR}, T_{QT})$-plane, where $f_{RR}=1/T_{RR}$ is the heart rate, on which the loop area is dimensionless. The total error-for Panel A is 2.2% and for Panel C is 0.8%.
Figure 20:
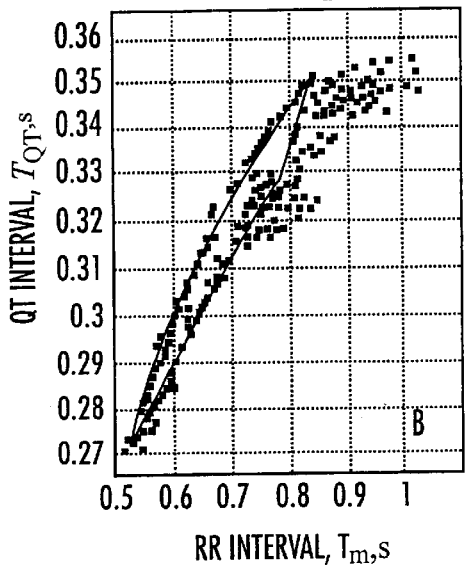
Figure 20:
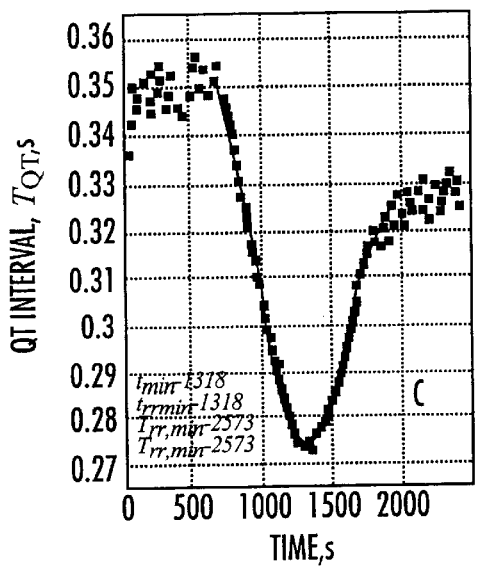
Figure 20:
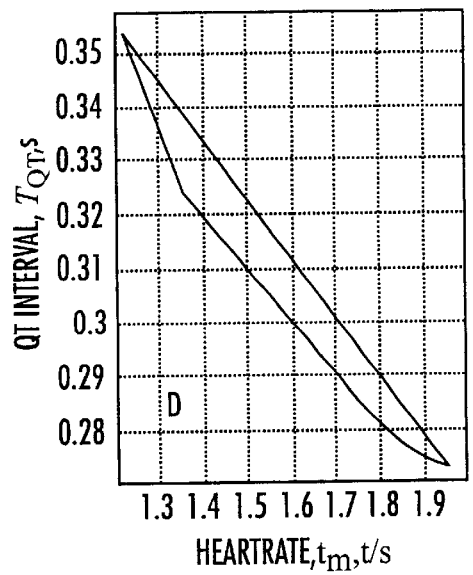

A similar dense representation of the descending branch can be calculated in exactly the same way. The resulting bird-like curves are illustrated in panels A and C of FIG. 20. The actual absolute and relative errors are indicated in the captions. The right hand side panels B and D represent hysteresis curves in two different representations and each resulting from the curves shown in Panels A and C. The following computations of the hysteresis loop and its measure given by Eq. (10.17) is then performed as described in Example 10.

EXAMPLE 13

Creation of an RR-Hysteresis Loop With the Procedures of Examples 10–12

In addition to the procedures generating a hysteresis loop on the plane (QT-interval versus RR-interval) or an equivalent plane, one can introduce and assess a separate hysteresis of the duration of RR-interval versus exercise workload, which gradually varies, there-and-back, during the ascending and descending exercise stages. The RR-hysteresis can be displayed as loops on different planes based on just a single RR data set $\{t_{RR}^i, T_{RR}^i\}$ analysis. For example, such a loop can be displayed on the $(\tau^i, T_{RR}^i)$-plane, where $\tau^i = |t_{RR}^i - t_{min}|$ and $t_{min}$ is the time instant corresponding to the peak of the exercise load, or the center of the maximum load period, which may be determined according to numerical techniques described in the examples 10–12. The RR loop can also be introduced on the $(W(t_{RR}^i), T_{RR}^i)$ or $(\tau^i, (T_{RR}^i)^{-1})$ planes. Here $W(t_{RR}^i)$ is a workload that varies versus exercise stages, i.e. time and $(T_{RR}^i)^{-1}$ represents the heart rate.

In order to apply a numerical technique from the Example 10 (or any other as in Examples 11 or 12), one repeats essentially the same computational steps described in these examples. However, instead of considering both QT-$\{t_{QT}^i, T_{QT}^i\}$ and RR-$\{t_{RR}^i, T_{RR}^i\}$ interval data sets, only a single RR data set is numerically processed throughout the whole sequence of the described stages for a creation of a hysteresis loop. In this case variables $\tau_i$, $(T_{RR}^i)^{-1}$ or $W(t_{RR}^i)$ play the role of the second alternating component that along with the first $T_{RR}^i$ variable forms the RR-hysteresis plane.

The foregoing examples are illustrative of the present invention and are not to be construed as limiting thereof. The invention is defined by the following claims, with equivalents of the claims to be included therein.

That which is claimed is:

1. A method of assessing cardiac isehemia in a subject to provide a measure of cardiac or cardiovascular health in that subject, said method comprising the steps of:

(a) collecting a first RR- interval data set from said subject during a stage of gradually increasing heart rate;

(b) collecting a second RR- interval data set from said subject during a stage of gradually decreasing heart rate, with said first and second RR- interval data sets being collected while minimizing the influence of rapid transients due to autonomic nervous system and hormonal influence on said data sets;

(c) comparing said first RR- interval data set to said second RR- interval data set to determine the difference between said data sets; and (d) generating from said comparison of step (c) a measure of cardiac ischemia in said subject, wherein a greater difference between said first and second data sets indicates greater cardiac ischemia and lesser cardiac or cardiovascular health in said subject;

wherein said first and second RR- interval data sets are collected by pulse or blood pressure monitoring.

2. The method according to claim 1, wherein said first and second RR-interval data sets are collected under quasi-stationary conditions.

3. The method according to claim 1, wherein said stage of gradually increasing heart rate and said stage of gradually decreasing heart rate are each at least 3 minutes in duration.

4. The method according to claim 1, wherein said stage of gradually increasing heart rate and said stage of gradually decreasing heart rate are together carried out for a total time of from 6 minutes to 40 minutes.

5. The method according to claim 1, wherein:

both said stage of gradually increasing heart rate and said stage of gradually decreasing heart rate are carried out between a peak rate and a minimum rate; and said peak rates of both said stage of gradually increasing heart rate and said stage of gradually decreasing heart rate are the same.

6. The method according to claim 5, wherein:

said minimum rates of both said stage of gradually increasing heart rate and said stage of gradually decreasing heart rate are substantially the same.

7. The method according to claim 1, wherein said stage of gradually decreasing heart rate is carried out at least three different heart-rate stimulation levels.

8. The method according to claim 7, wherein said stage of gradually increasing heart rate is carried out at least three different heart-rate stimulation levels.

9. The method according to claim 1, wherein said stage of gradually increasing heart rate and said stage of gradually decreasing heart rate are carried out sequentially in time.

10. The method according to claim 1, wherein said comparing step is carried out by generating curves from each of said data sets.

11. The method according to claim 10, wherein said comparing step is carried out by comparing the shapes of said curves from data sets.

12. The method according to claim 10, wherein said comparing step is carried out by determining a measure of the domain between said curves.

13. The method according to claim 10, wherein said comparing step is carried out by both comparing the shapes of said curves from data sets and determining a measure of the domain between said curves.

14. The method according to claim 10, further comprising the step of displaying said curves.

15. The method according to claim 1, wherein said heart rate during said stage of gradually increasing heart rate does not exceed more than 120 beats per minute.

16. The method according to claim 1, wherein said heart rate during said stage of gradually increasing heart rate exceeds 120 beats per minute.

17. The method according to claim 1, further comprising the step of:

(e) comparing said measure of cardiac ischemia during stimulation to at least one reference value; and then (f) generating from said comparison of step (e) a quantitative indicium of cardiac or cardiovascular health for said subject.

18. The method according to claim 17, further comprising the steps of:

(g) treating said subject with a cardiovascular therapy; and then (h) repeating steps (a) through (f) to assess the efficacy of said cardiovascular therapy, in which a decrease in the difference between said data sets from before said therapy to after said therapy indicates an improvement in cardiac health in said subject from said cardiovascular therapy.

19. The method according to claim 18, wherein said cardiovascular therapy is selected from the group consisting of aerobic exercise, muscle strength building, change in diet, nutritional supplement, weight loss, stress reduction, smoking cessation, pharmaceutical treatment, surgical treatment, and combinations thereof.

20. The method according to claim 17, further comprising the step of assessing from said quantitative indicium the likelihood that said subject is at risk to experience a future ischemia-related cardiac incident.

21. A method of assessing cardiac ischemia in a subject to provide a measure of cardiac or cardiovascular health in that subject, said method comprising the steps of:

(a) collecting a first RR-interval data set from said subject during a stage of gradually increasing exercise load and gradually increasing heart rate; and then, without an intervening rest stage, (b) collecting a second RR-interval data set from said subject during a stage of gradually decreasing exercise load and gradually decreasing heart rate;

(c) comparing said first RR-interval data set to said second RR-interval data set to determine the difference between said data sets; and (d) generating from said comparison of step (c) a measure of cardiac ischemia during exercise in said subject, wherein a greater difference between said first and second data sets indicates greater cardiac ischemia and lesser cardiac or cardiovascular health in said subject;

wherein said first and second RR-interval data sets are collected by pulse or blood pressure monitoring.

22. The method according to claim 21, wherein said stage of gradually increasing exercise load and gradually decreasing exercise load are each at least 3 minutes in duration.

23. The method according to claim 21, wherein said stage of gradually increasing exercise load and said stage of gradually decreasing exercise load are together carried out for a total time of from 6 minutes to 40 minutes.

24. The method according to claim 21, wherein:

both said stage of gradually increasing exercise load and said stage of gradually decreasing exercise load are carried out between a peak load and a minimum load; and said peak loads of both said stage of gradually increasing exercise load and said stage of gradually decreasing exercise load are essentially the same.

25. The method according to claim 24, wherein:

said minimum loads of both said stage of gradually increasing exercise load and said stage of gradually decreasing exercise load are essentially the same.

26. The method according to claim 21, wherein said stage of gradually decreasing exercise load is carried out at least three different load levels.

27. The method according to claim 21, wherein said stage of gradually increasing exercise load is carried out at least three different load levels.

28. The method according to claim 21, wherein said stage of gradually increasing exercise load and said stage of gradually decreasing exercise load are carried out sequentially in time.

29. The method according to claim 21, wherein said comparing step is carried out by generating curves from each of said data sets.

30. The method according to claim 29, wherein said comparing step is carried out by comparing the shapes of said curves from said data sets.

31. The method according to claim 29, wherein said comparing step is carried out by determining a measure of the domain between said curves.

32. The method according to claim 29, wherein said comparing step is carried out by both comparing the shapes of said curves from data sets and determining a measure of the domain between said curves.

33. The method according to claim 29, further comprising the step of displaying said curves.

34. The method according to claim 21, wherein said heart rate during said stage of gradually increasing exercise load does not exceed more than 120 beats per minute.

35. The method according to claim 21, wherein said heart rate during said stage of gradually increasing heart rate exceeds 120 beats per minute.

36. The method according to claim 21, further comprising the step of:
   (e) comparing said measure of cardiac ischemia during exercise to at least one reference value; and then
   (f) generating from said comparison of step (e) a quantitative indicium of cardiac or cardiovascular health for said subject.

37. The method according to claim 36, further comprising the steps of:
   (g) treating said subject with a cardiovascular therapy; and then
   (h) repeating steps (a) through (f) to assess the efficacy of said cardiovascular therapy, in which a decrease in the difference between said data sets from before said therapy to after said therapy indicates an improvement in cardiac or cardiovascular health in said subject from said cardiovascular therapy.

38. The method according to claim 37, wherein said cardiovascular therapy is selected from the group consisting of aerobic exercise, muscle strength building, change in diet, nutritional supplement, weight loss, stress reduction, smoking cessation, pharmaceutical treatment, surgical treatment, and combinations thereof.

39. The method according to claim 36, further comprising the step of assessing from said quantitative indicium the likelihood that said subject is at risk to experience a future ischemia-related cardiac incident.

40. A method of assessing cardiac ischemia in a subject to provide a measure of cardiac or cardiovascular health in that subject, said method comprising the steps, performed on a computer system, of:
   (a) providing a first RR- interval data set collected from said subject during a stage of gradually increasing heart rate;
   (b) providing a second RR- interval data set collected from said subject during a stage of gradually decreasing heart rate;
   (c) comparing said first RR- interval data set to said second RR- interval data set to determine the difference between said data sets; and
   (d) generating from said comparison of step (c) a measure of cardiac ischemia in said subject, wherein a greater difference between said first and second data sets indicates greater cardiac ischemia and lesser cardiac or cardiovascular health in said subject;
   wherein said first and second RR- interval data sets comprise pulse or blood pressure data sets.

41. The method according to claim 40, wherein said first and second RR-interval data sets are collected while minimizing the influence of rapid transients due to autonomic nervous system and hormonal control on said data sets.

42. The method according to claim 40, wherein said first and second RR-interval data sets are collected without an intervening rest stage.

43. The method according to claim 40, wherein said comparing step is carried out by generating curves from each of said data sets.

44. The method according to claim 43, wherein said comparing step is carried out by comparing the shapes of said curves from data sets.

45. The method according to claim 43, wherein said comparing step is carried out by determining a measure of the domain between said curves.

46. The method according to claim 43, wherein said comparing step is carried out by both comparing the shapes of said curves from data sets and determining a measure of the domain between said curves.

47. The method according to claim 43, further comprising the step of displaying said curves.

48. The method according to claim 40, wherein said comparing step is carried out by:
   (i) filtering said first and second RR-interval data sets;
   (ii) generating a smoothed hysteresis loop from said filtered first and second RR-interval data sets; and then
   (iii) determining the domain of said smoothed hysteresis loop.

49. The method according to claim 40, wherein said comparing step is carried out by:
   (i) filtering said first and second RR-interval data sets;
   (ii) generating preliminary minima values for said first and second RR-interval data sets;
   (iii) correcting said preliminary minima values;
   (iv) generating first and second preliminary smoothed curves from each of said filtered data sets;
   (v) correcting said preliminary smoothed curves;
   (vi) fitting said preliminary smoothed curves;
   (vii) generating a smoothed hysteresis loop from said first and second fitted smoothed curves; and then
   (viii) determining the domain of said hysteresis loop.

50. The method according to claim 40, wherein said comparing step is carried out by:
   (i) filtering said first and second RR-interval data sets by moving average smoothing;
   (ii) generating a smoothed hysteresis loop from said filtered first and second RR-interval data sets; and then
   (iii) determining the domain of said hysteresis loop.

51. The method according to claim 40, wherein said comparing step is carried out by
   (i) sequentially combining said first and second RR-interval data sets into one combined RR-interval set;

(ii) filtering said combined RR-interval data sets;

(iii) evaluating coordinates of the minima of said combined and filtered RR-interval data set;

(iv) defining central data subsets including the minima of said combined and filtered RR-interval data set;

(v) fitting each said central data subset with a parabola that has a minimum inside said data subset;

(vi) determining coordinates of the minimum for each said parabola;

(vii) defining reduced data subsets by excluding said central data sets from said combined and filtered RR-interval data set;

(viii) generating a first transformed RR-interval data set by mapping falling off branches of said reduced data sets by a standard monotonously decreasing mapping function of RR-intervals, which depends on at least one discrete or continuous parameter;

(ix) generating a second transformed RR-interval data set by mapping growing branches of said reduced data sets by a standard monotonously increasing mapping function of RR-intervals, which depends on at least one discrete or continuous parameter;

(x) fitting said first and second transformed sets by a standard function of time depending on one or more parameters whose values are determined by the condition of the best fit;

(xi) completing said fitting step by determining the parameters of said mapping functions of RR-intervals by the condition of the best fit for each branch of said RR-interval data set;

(xii) generating a hysteresis loop from said best fit functions; and then (xiii) evaluating a measure of the domain inside said hysteresis loop.

52. A computer system for assessing cardiac isehemia in a subject to provide a measure of cardiac or cardiovascular health in that subject, said system comprising:

(a) means for providing a first RR- interval data set from said subject during a stage of gradually increasing heart rate;

(b) means for providing a second RR- interval data set from said subject during a stage of gradually decreasing heart rate;

(c) means for comparing said first RR- interval data set to said second RR- interval data set to determine the difference between said data sets; and (d) means for generating from said comparison a measure of cardiac ischemia in said subject, wherein a greater difference between said first and second data sets indicates greater cardiac ischemia and lesser cardiac or cardiovascular health in said subject;

(e) means for comparing the measure of cardiac ischemia to at least one reference value; and (f) means for generating at least one quantiative indicium of cardiovascular health for said subject;

wherein said first and second RR- interval data sets comprise pulse or blood pressure data sets.

53. The system according to claim 52, wherein said comparing means further comprises means for generating curves from each of said data sets.

54. The system according to claim 53, wherein said comparing means further comprises means for comparing the shapes of said curves from data sets.

55. The system according to claim 53, wherein said comparing means further comprises means for determining a measure of the domain between said curves.

56. The system according to claim 53, wherein said comparing means further comprises means for both comparing the shapes of said curves from data sets and determining a measure of the domain between said curves.

* * * * *

UNITED STATES PATENT AND TRADEMARK OFFICE
CERTIFICATE OF CORRECTION

PATENT NO. : 6,656,126 B2
DATED : December 2, 2003
INVENTOR(S) : Starobin et al.

It is certified that error appears in the above-identified patent and that said Letters Patent is hereby corrected as shown below:

<u>Column 32,</u>
Line 31, should read --
$$t_i^- = t_i - t_{min}, \quad t_i \leq 0,$$
$$t_j^+ = t_j - t_{min} \quad t_j > 0. \qquad (12.8)$$
--

<u>Column 33,</u>
Line 2, should read -- from which the condition $y_j \geq 1$ is satisfied for all subsequent --

Line 55, should read -- $u_{\gamma,j}^+ = g_\gamma^+ \left( y_j^+ \right)$ \qquad (12.13) --

<u>Column 34,</u>
Line 59, should read -- $v_k = 1 - u_k^-$. \qquad (12.20) --

<u>Column 35,</u>
Line 6, should read -- where the function φ depends linearly on K and is defined --

Line 44, should read -- $\varepsilon^{(\omega)}(K,\alpha,\beta) = \sum_{k \leq K_t} \left[ u_k - K\varphi(\alpha, \beta, T_k) \right]^2$ \qquad (12.24) --

<u>Column 37,</u>
Line 39, should read -- gradually decreasing heart rate is carried out at at least three --
Line 42, should read -- gradually increasing heart rate is carried out at at least three --

<u>Column 39,</u>
Line 2, should read -- of gradually decreasing exercise load is carried out at at least --
Line 5, should read -- of gradually increasing exercise load is carried out at at least --
Line 58, should read -- 40. A method of assessing cardiac ischemia in a subject to --

<u>Column 41,</u>
Line 37, should read -- 52. A computer system for assessing cardiac ischemia in --

UNITED STATES PATENT AND TRADEMARK OFFICE
CERTIFICATE OF CORRECTION

PATENT NO.    : 6,656,126 B2
DATED         : December 2, 2003
INVENTOR(S)   : Starobin et al.

It is certified that error appears in the above-identified patent and that said Letters Patent is hereby corrected as shown below:

Column 42,
Line 19, should read -- (*f*) means for generating at least one quantitative indicium --

Signed and Sealed this

Sixth Day of April, 2004

JON W. DUDAS
*Acting Director of the United States Patent and Trademark Office*